(12) United States Patent
Parker et al.

(10) Patent No.: US 6,504,985 B2
(45) Date of Patent: Jan. 7, 2003

(54) ILLUMINATED SURGICAL RETRACTOR

(75) Inventors: Jeffery R. Parker, Strongsville, OH (US); Jeffrey B. Williams, Ravenna, OH (US); Robert Caywood, Vermilion, OH (US)

(73) Assignee: Lumitex, Inc., Strongsville, OH (US)

( * ) Notice: Subject to any disclaimer, the term of this patent is extended or adjusted under 35 U.S.C. 154(b) by 91 days.

(21) Appl. No.: 09/735,104

(22) Filed: Dec. 12, 2000

(65) Prior Publication Data

US 2001/0001260 A1 May 17, 2001

Related U.S. Application Data

(60) Continuation of application No. 09/120,406, filed on Jul. 22, 1998, now Pat. No. 6,185,356, and a division of application No. 08/778,180, filed on Jan. 2, 1997, now Pat. No. 5,921,652, and a division of application No. 08/778,734, filed on Jan. 2, 1997, now Pat. No. 5,876,107, which is a division of application No. 08/495,176, filed on Jun. 27, 1995, now Pat. No. 5,613,751, said application No. 09/120,406, is a continuation-in-part of application No. 08/886,666, filed on Jul. 2, 1997, which is a continuation-in-part of application No. 08/778,089, filed on Jan. 2, 1997, now Pat. No. 6,079,838, which is a division of application No. 08/495,176, said application No. 08/778,180, is a division of application No. 08/495,176.

(51) Int. Cl.⁷ ............................................. G02B 6/20
(52) U.S. Cl. ..................... 385/133; 385/125; 385/901; 362/559
(58) Field of Search ............................... 385/133, 125, 385/901, 902, 146; 362/551, 559, 562, 578

(56) References Cited

U.S. PATENT DOCUMENTS

| | | | |
|---|---|---|---|
| 3,328,570 A | 6/1967 | Balchunas | 362/31 |
| 3,638,644 A * | 2/1972 | Reick | 600/191 |
| 3,680,546 A | 8/1972 | Asrican | 600/219 |
| 3,712,705 A | 1/1973 | Marcatili | 385/125 |
| 3,807,393 A | 4/1974 | McDonald | 600/208 |
| 3,890,960 A | 6/1975 | Wunsch et al. | 600/901 |
| 3,901,674 A | 8/1975 | Stack et al. | 65/412 |
| 3,950,073 A | 4/1976 | Horiguchi et al. | 385/123 |
| 4,043,636 A | 8/1977 | Eberhardt et al. | 349/65 |
| 4,052,980 A | 10/1977 | Grams et al. | 600/224 |
| 4,226,228 A | 10/1980 | Shin et al. | 600/206 |
| 4,337,763 A | 7/1982 | Petrassevich | 600/210 |
| 4,471,412 A | 9/1984 | Mori | 362/565 |
| 4,562,832 A | 1/1986 | Wilder et al. | 600/223 |
| 4,597,030 A * | 6/1986 | Brody et al. | 362/572 |
| 4,686,972 A | 8/1987 | Kurland | 606/96 |
| 4,714,983 A | 12/1987 | Lang | 362/27 |
| 4,733,332 A | 3/1988 | Yamashita et al. | 362/582 |

(List continued on next page.)

FOREIGN PATENT DOCUMENTS

| | | |
|---|---|---|
| DE | 86 00 868 | 4/1986 |
| DE | 86 07 483 | 7/1986 |
| DE | 4234050 A1 | 6/1993 |
| WO | PCT/US95/15117 | 6/1996 |
| WO | PCT/US96/07512 | 11/1996 |

OTHER PUBLICATIONS

General Surgery & Laparoscopy News, Bioenterics Corporation—EndoLumina II Illuminated Bougie, Aug. 1997.

*Primary Examiner*—Hung N. Ngo
(74) *Attorney, Agent, or Firm*—Renner, Otto, Boisselle & Sklar, LLP

(57) ABSTRACT

An illuminated surgical retractor includes a handle having an elongated first blade portion connected at one end to one end of the handle and an elongated second blade portion extending along the length of the first blade portion. One end of the second blade portion defines an illumination input end to which a connector is coupled. The connector is shaped to optically couple the illumination input end to a source of illumination so that at least a portion of one of the first and second blade portions is illuminated.

40 Claims, 25 Drawing Sheets

U.S. PATENT DOCUMENTS

| | | |
|---|---|---|
| 4,765,701 A | 8/1988 | Cheslak ........................ 362/560 |
| 4,785,796 A | 11/1988 | Mattson ....................... 600/200 |
| 4,790,751 A | 12/1988 | Reinhardt et al. ............. 433/29 |
| 4,790,752 A | 12/1988 | Cheslak ........................ 433/37 |
| 4,807,599 A | 2/1989 | Robinson et al. ............ 600/212 |
| 4,968,124 A | 11/1990 | Deckert et al. .............. 359/435 |
| 4,974,122 A | 11/1990 | Shaw ............................ 362/31 |
| 5,005,108 A | 4/1991 | Pristash et al. ................ 362/31 |
| 5,035,232 A | 7/1991 | Lutze et al. ................. 600/213 |
| 5,039,198 A | 8/1991 | VanBeek .................... 385/117 |
| 5,052,778 A | 10/1991 | Jamshid ...................... 385/125 |
| 5,097,396 A | 3/1992 | Myers ......................... 362/551 |
| 5,136,480 A | 8/1992 | Pristash et al. ................ 362/31 |
| 5,159,921 A | 11/1992 | Hoover ....................... 600/207 |
| 5,209,757 A | 5/1993 | Krug et al. .................. 606/162 |
| 5,226,105 A | 7/1993 | Myers ......................... 385/147 |
| 5,237,985 A | 8/1993 | Hodgson et al. ............. 600/205 |
| 5,281,134 A | 1/1994 | Schultz ......................... 433/29 |
| 5,295,216 A | 3/1994 | Halter ......................... 385/120 |
| 5,303,323 A | 4/1994 | Mezei ......................... 385/147 |
| 5,307,245 A | 4/1994 | Myers et al. ................ 362/554 |
| 5,312,569 A | 5/1994 | Mezei ......................... 264/1.24 |
| 5,312,570 A | 5/1994 | Halter ......................... 264/1.24 |
| 5,394,863 A | 3/1995 | Sanford et al. .............. 600/199 |
| 5,431,153 A | 7/1995 | Lee ............................. 600/183 |
| 5,499,912 A | 3/1996 | Mezei ......................... 425/362 |
| 5,520,611 A | 5/1996 | Rao et al. .................... 600/245 |
| 5,571,215 A | 11/1996 | Sterman et al. ............. 600/102 |
| 5,618,096 A | 4/1997 | Parker et al. .................. 362/31 |
| 5,982,969 A | 11/1999 | Sugiyama et al. ........... 385/123 |

\* cited by examiner

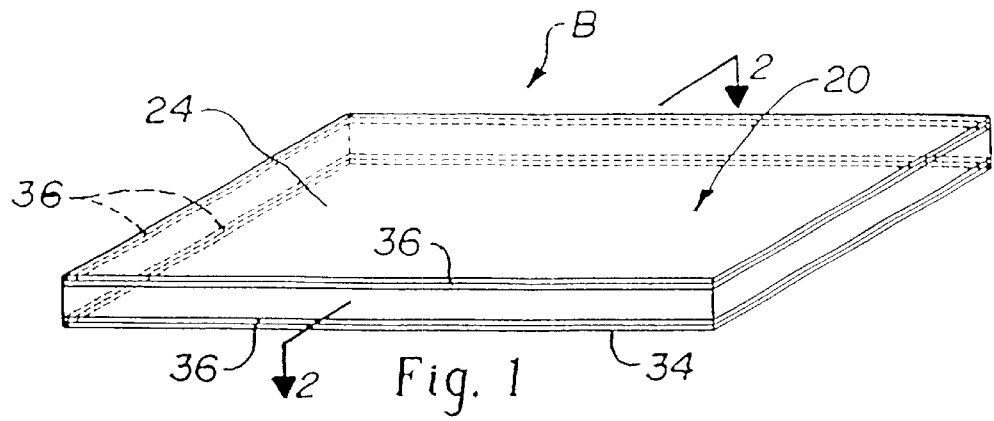
Fig. 1
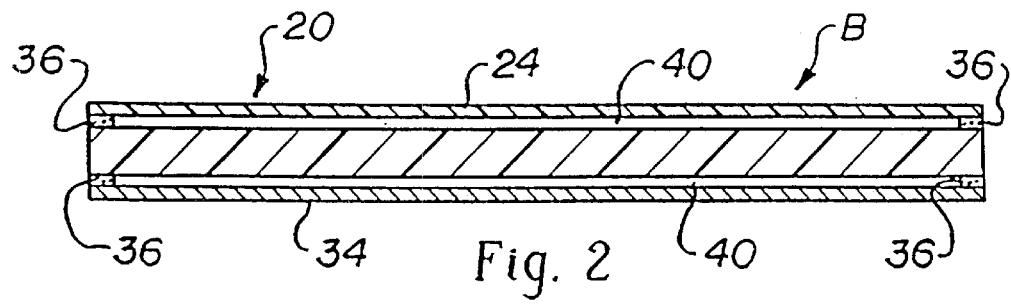
Fig. 2
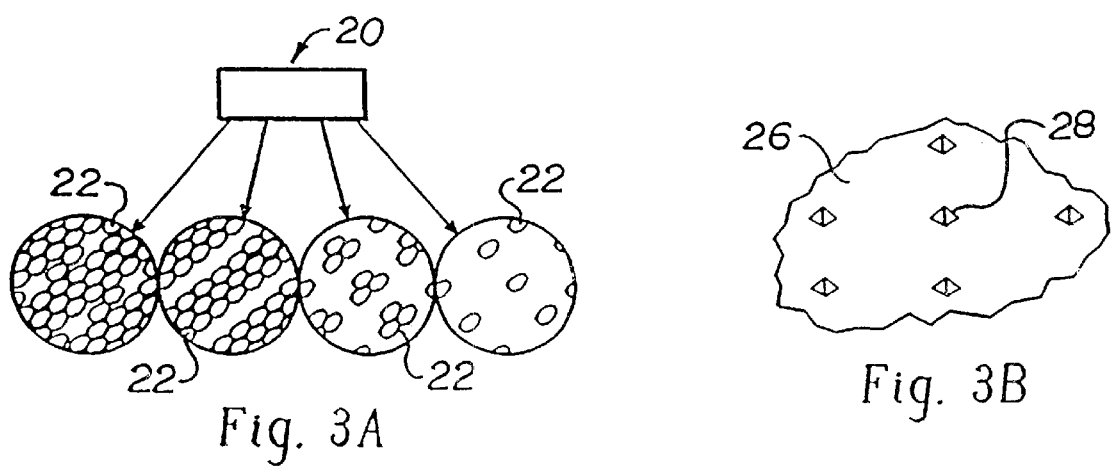
Fig. 3A
Fig. 3B
Fig. 3C
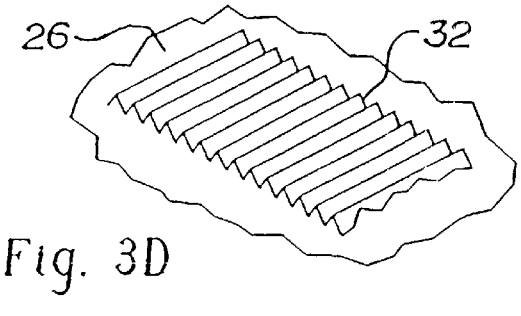
Fig. 3D

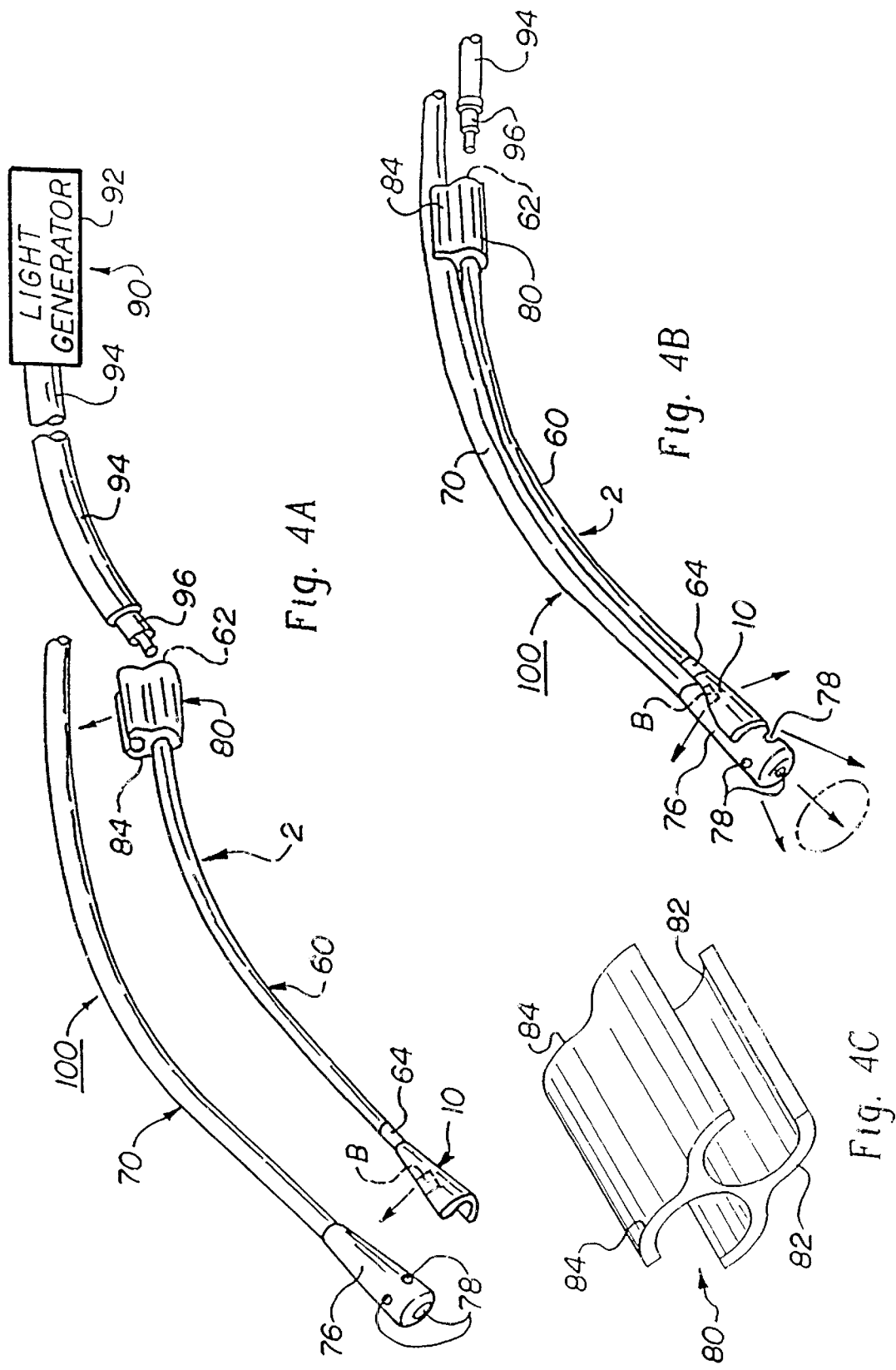

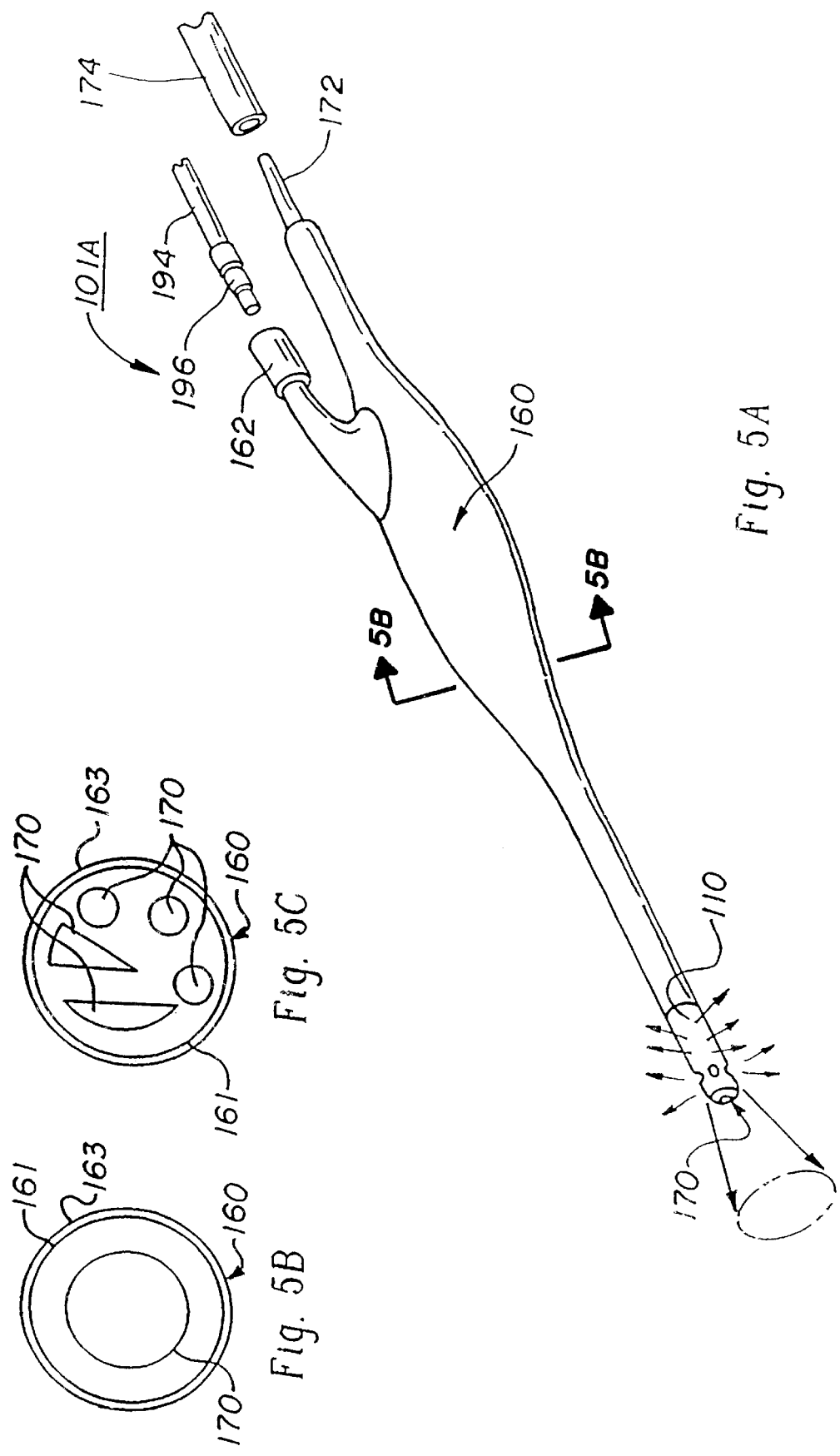

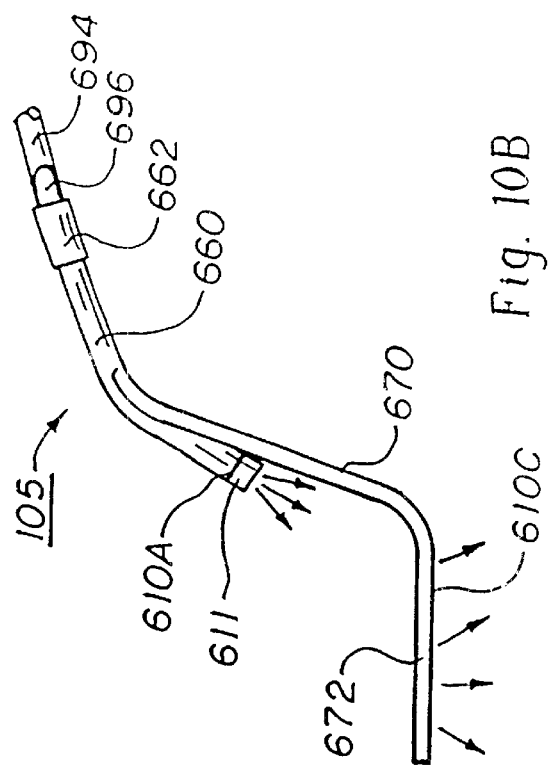
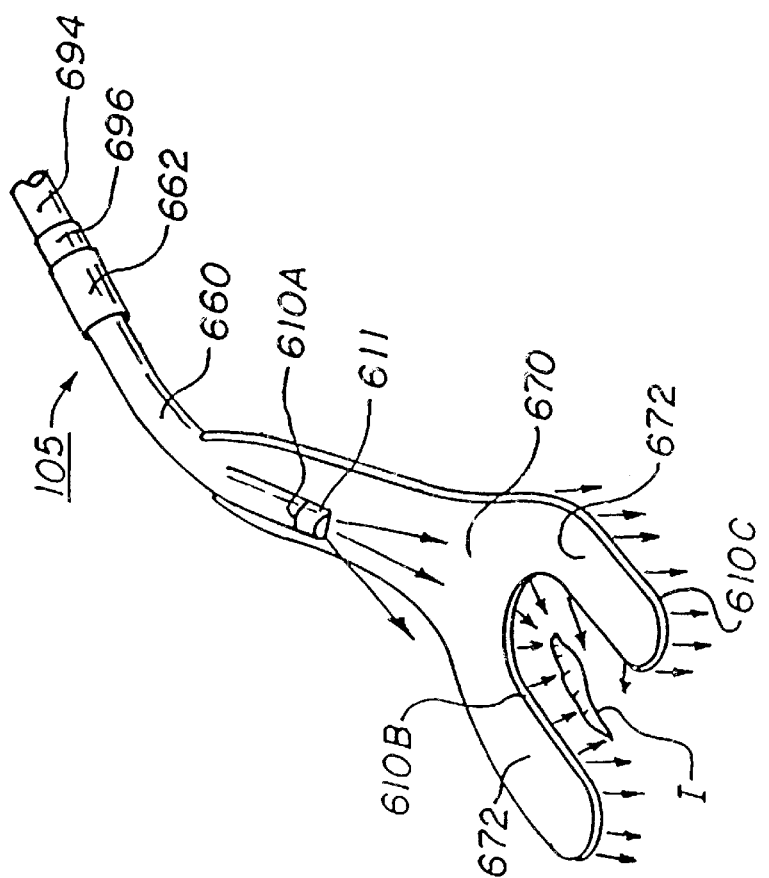
Fig. 10B
Fig. 10A

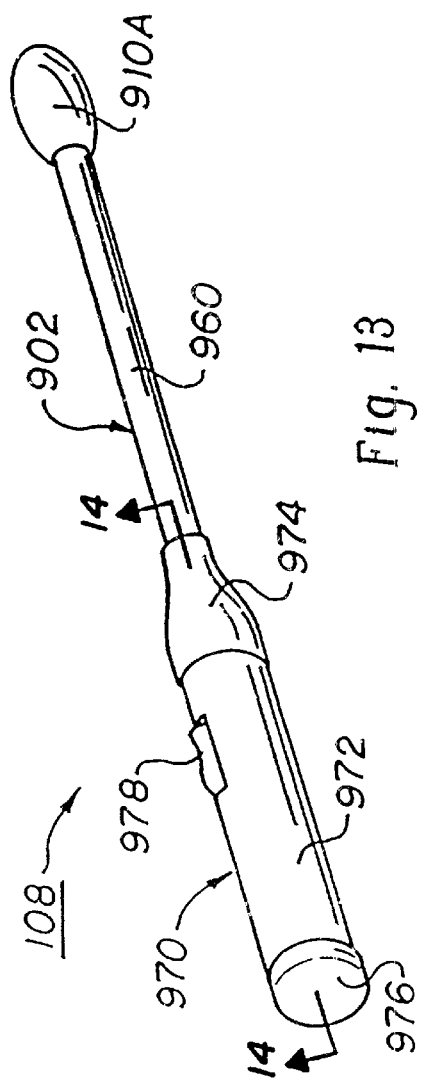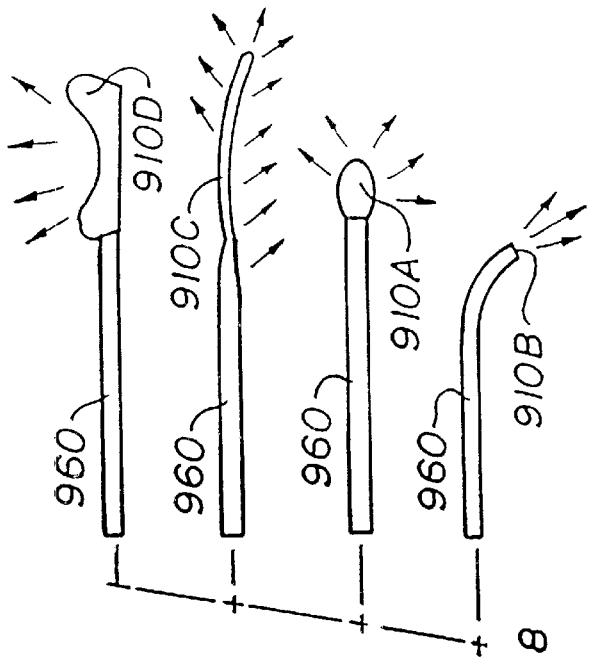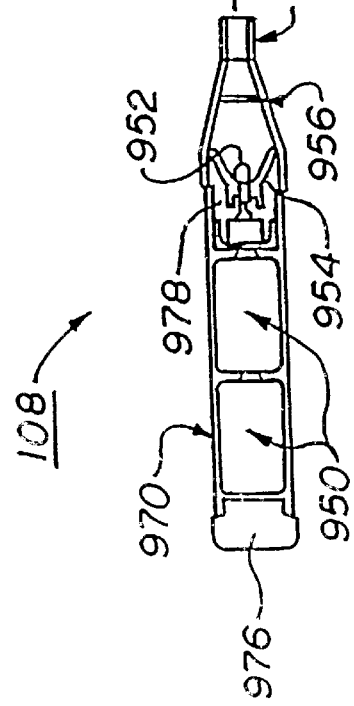
Fig. 13
Fig. 14

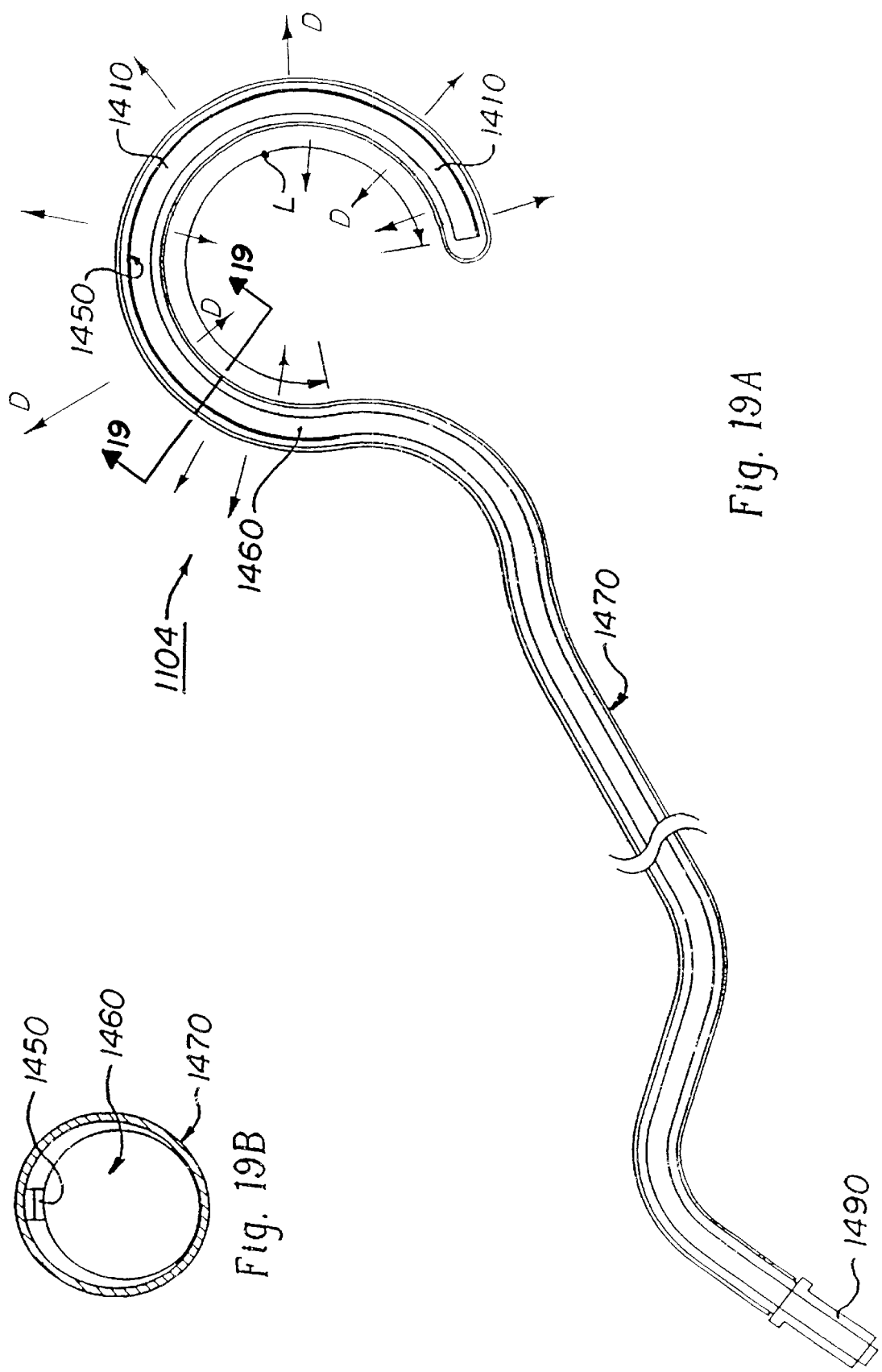

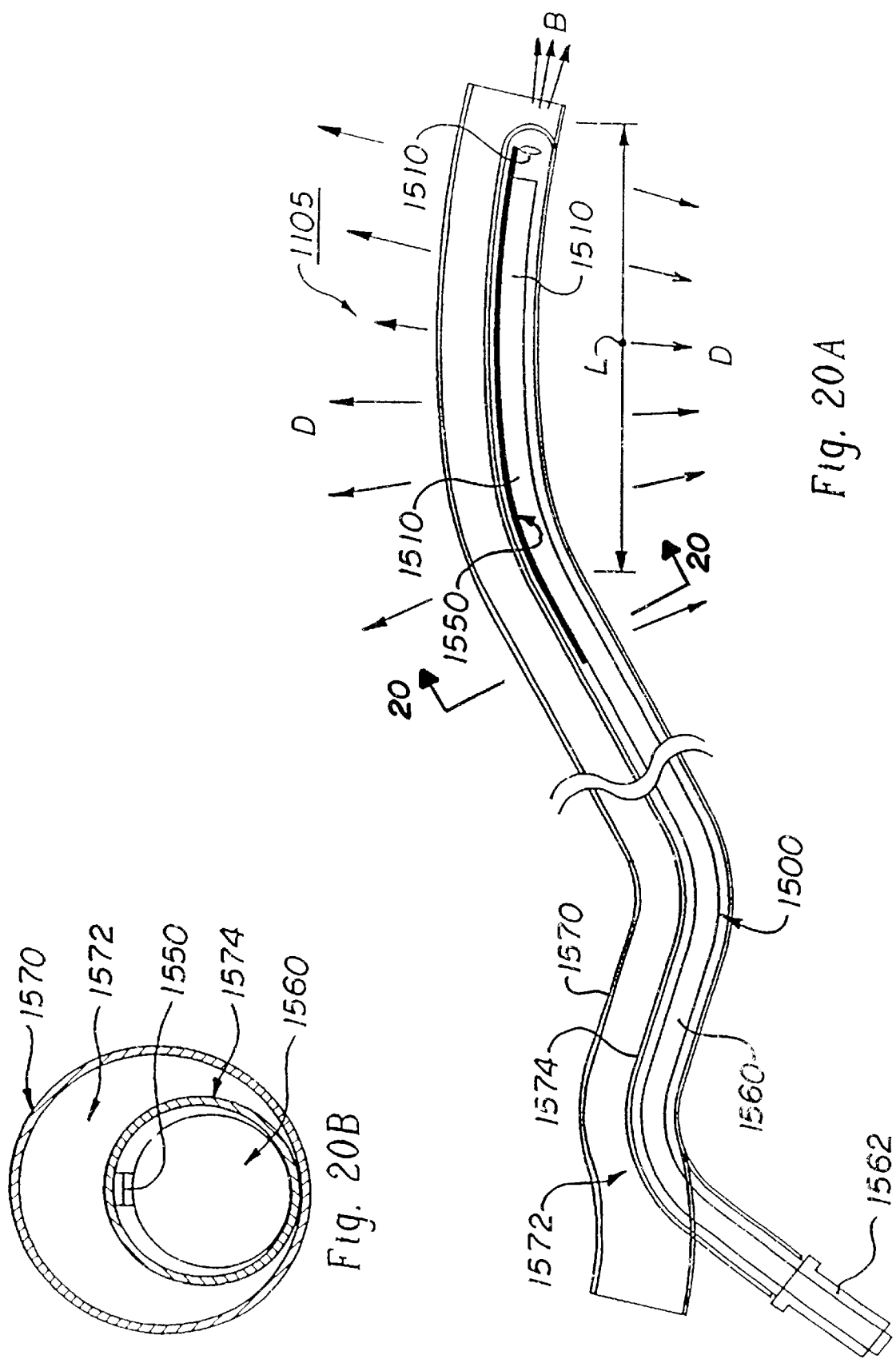

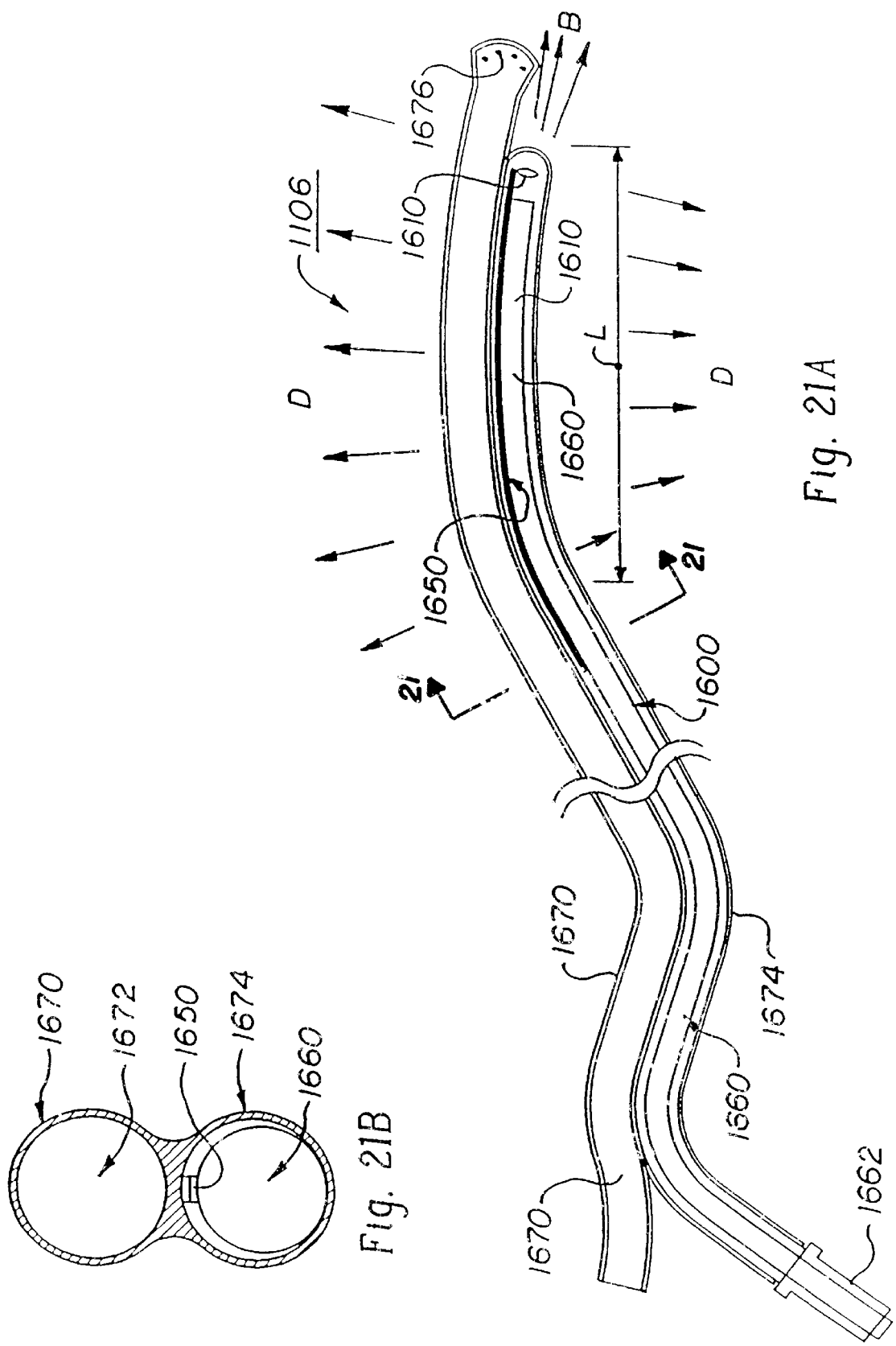

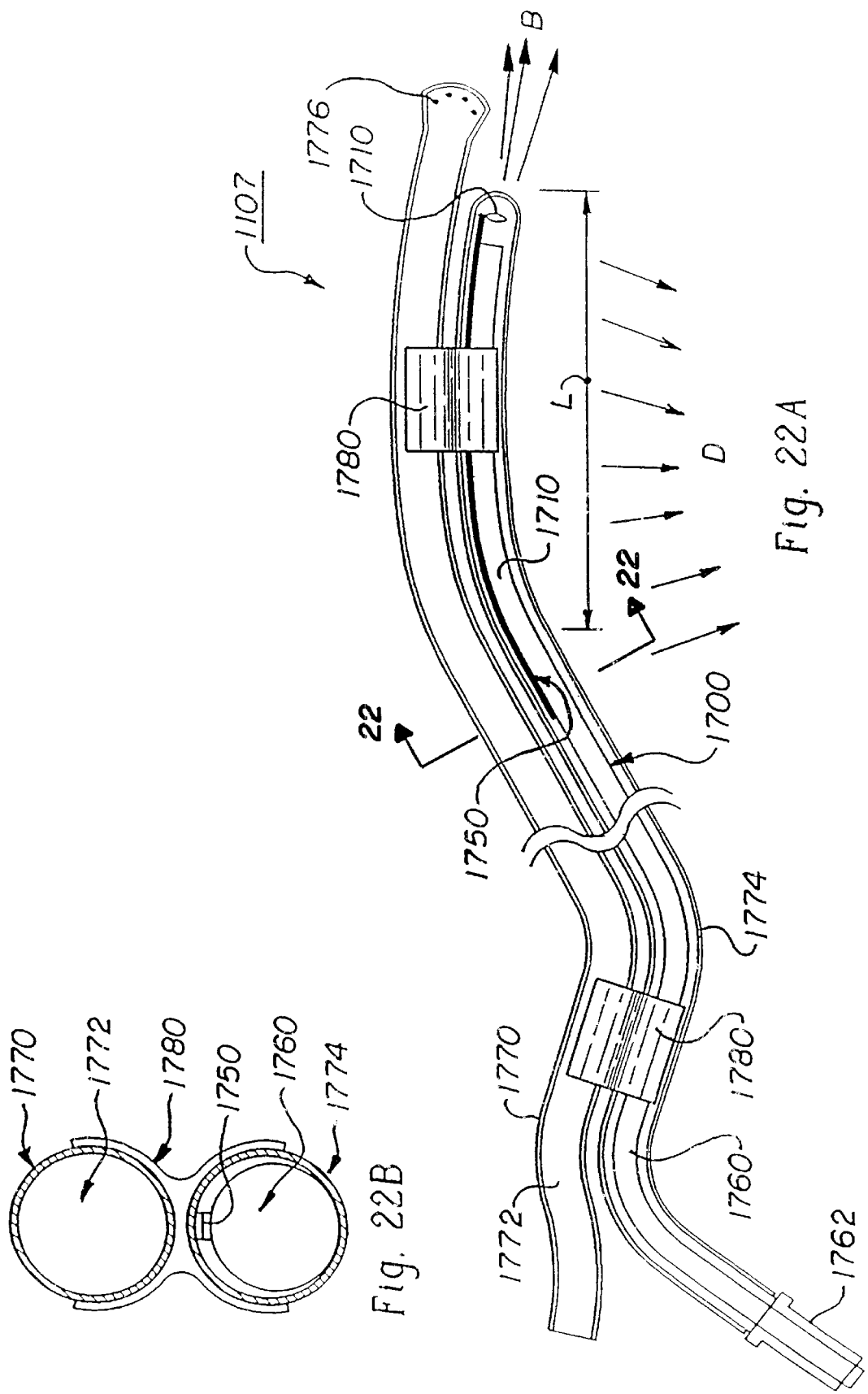

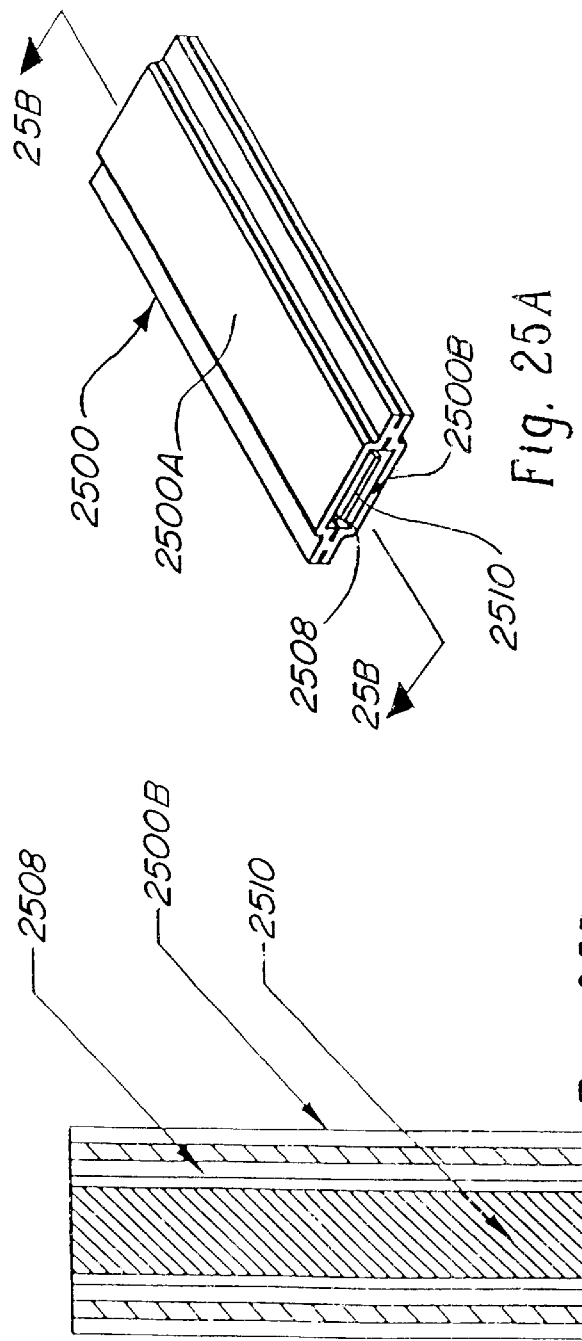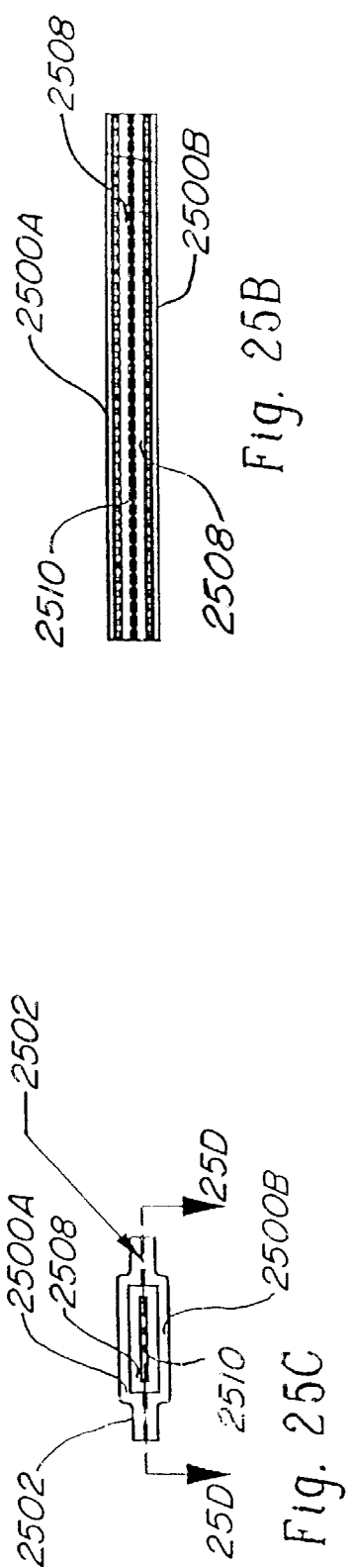

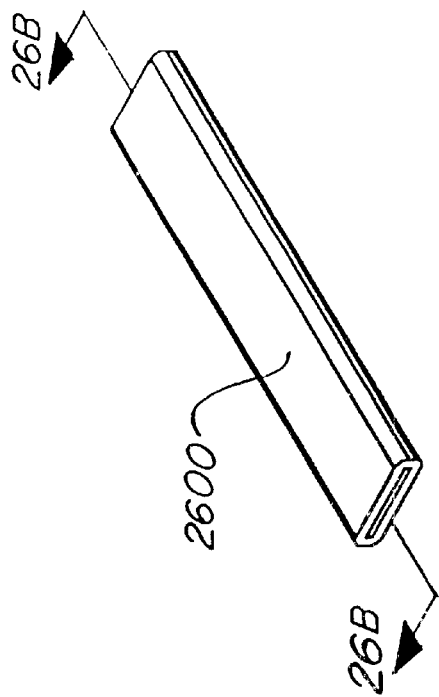
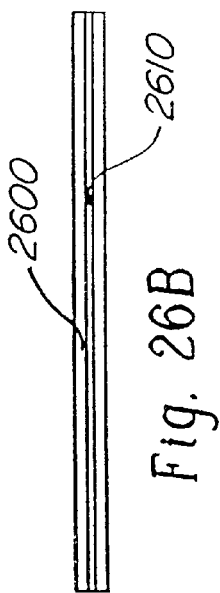
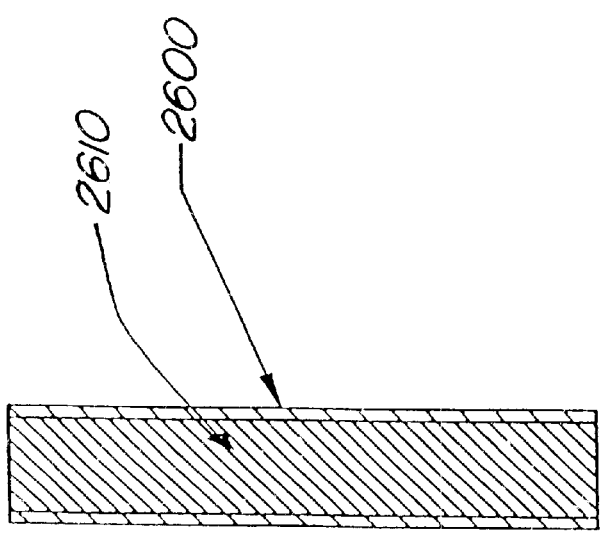
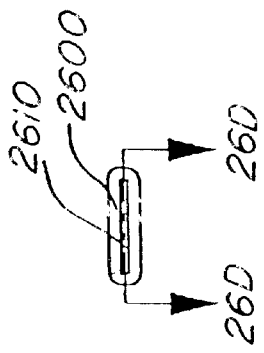

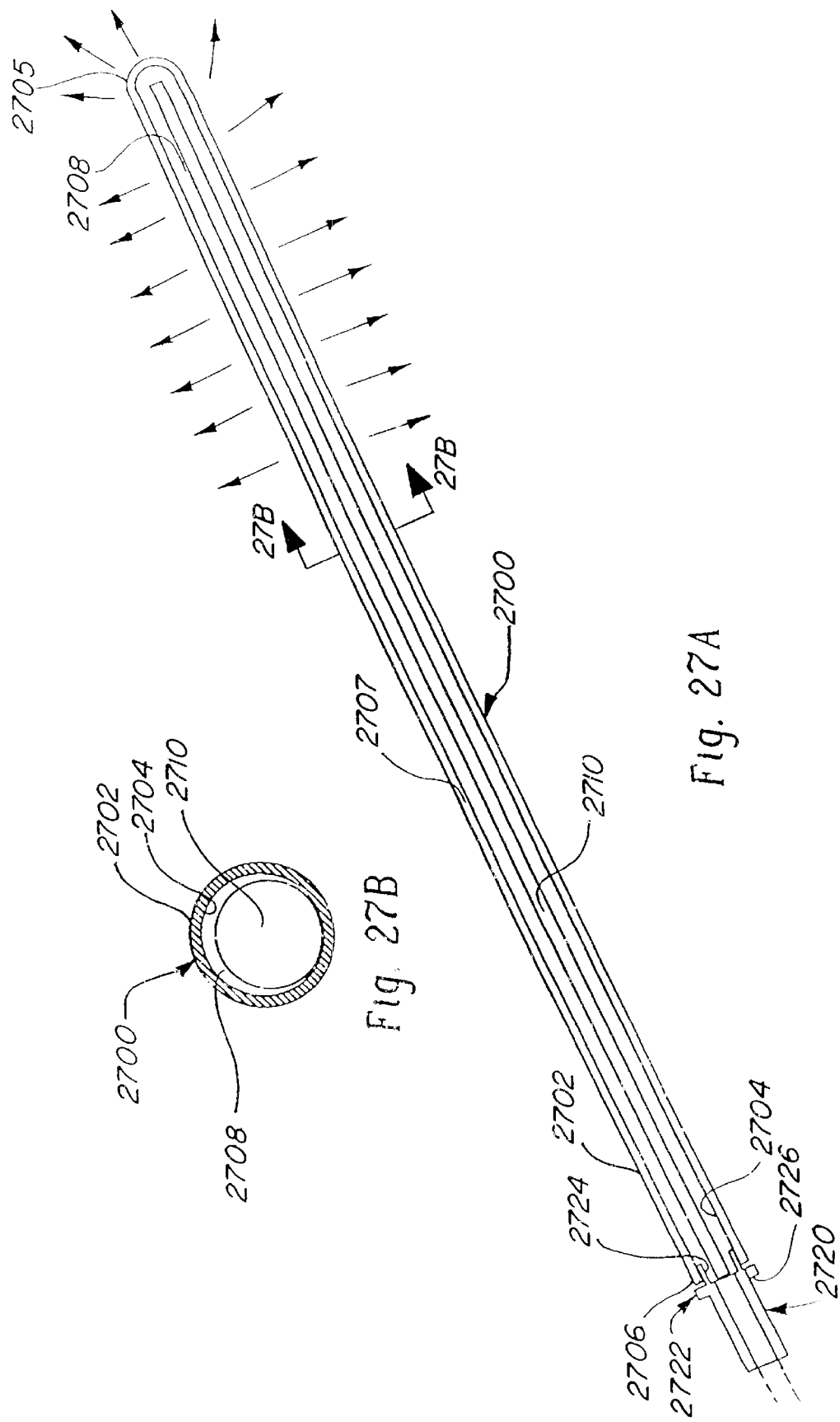

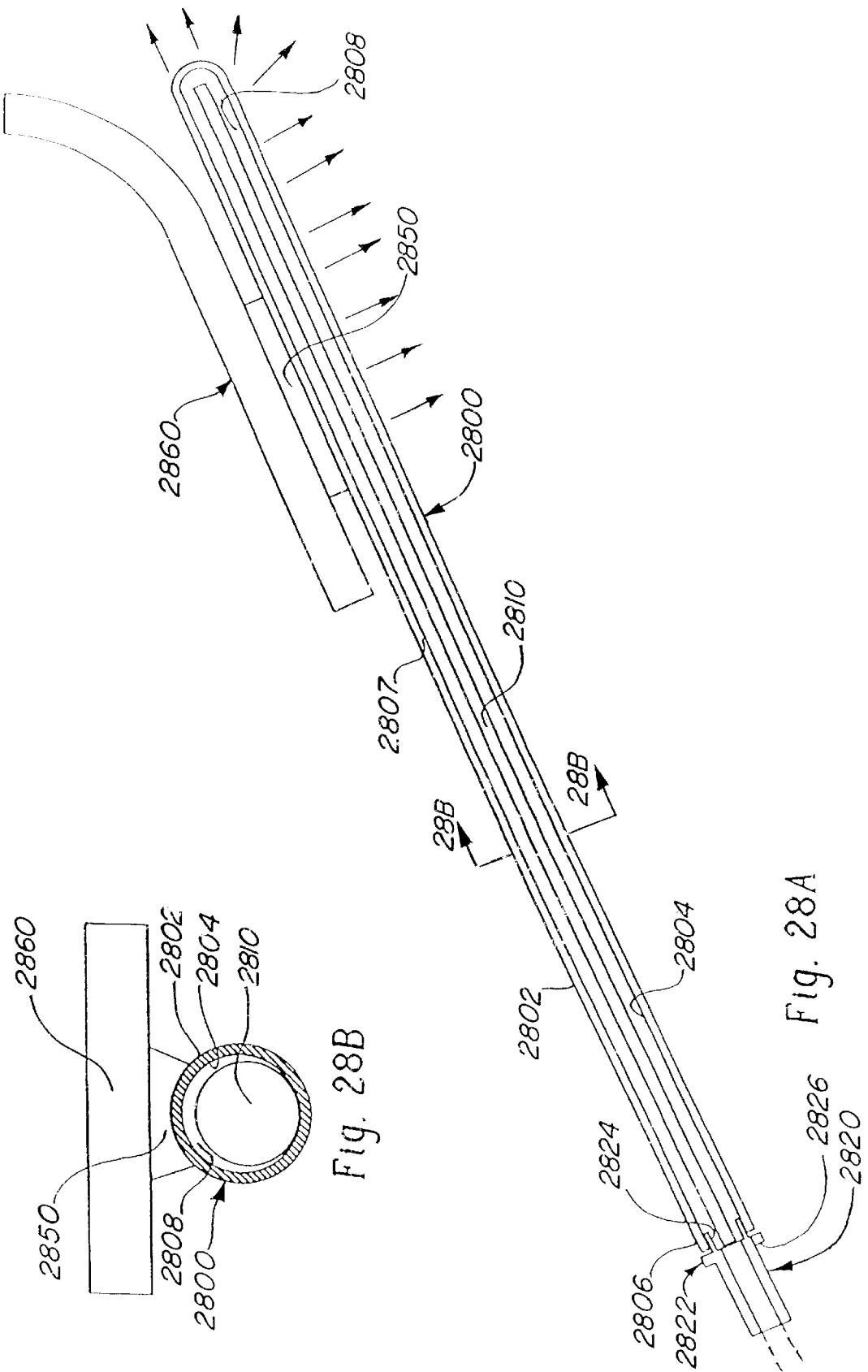

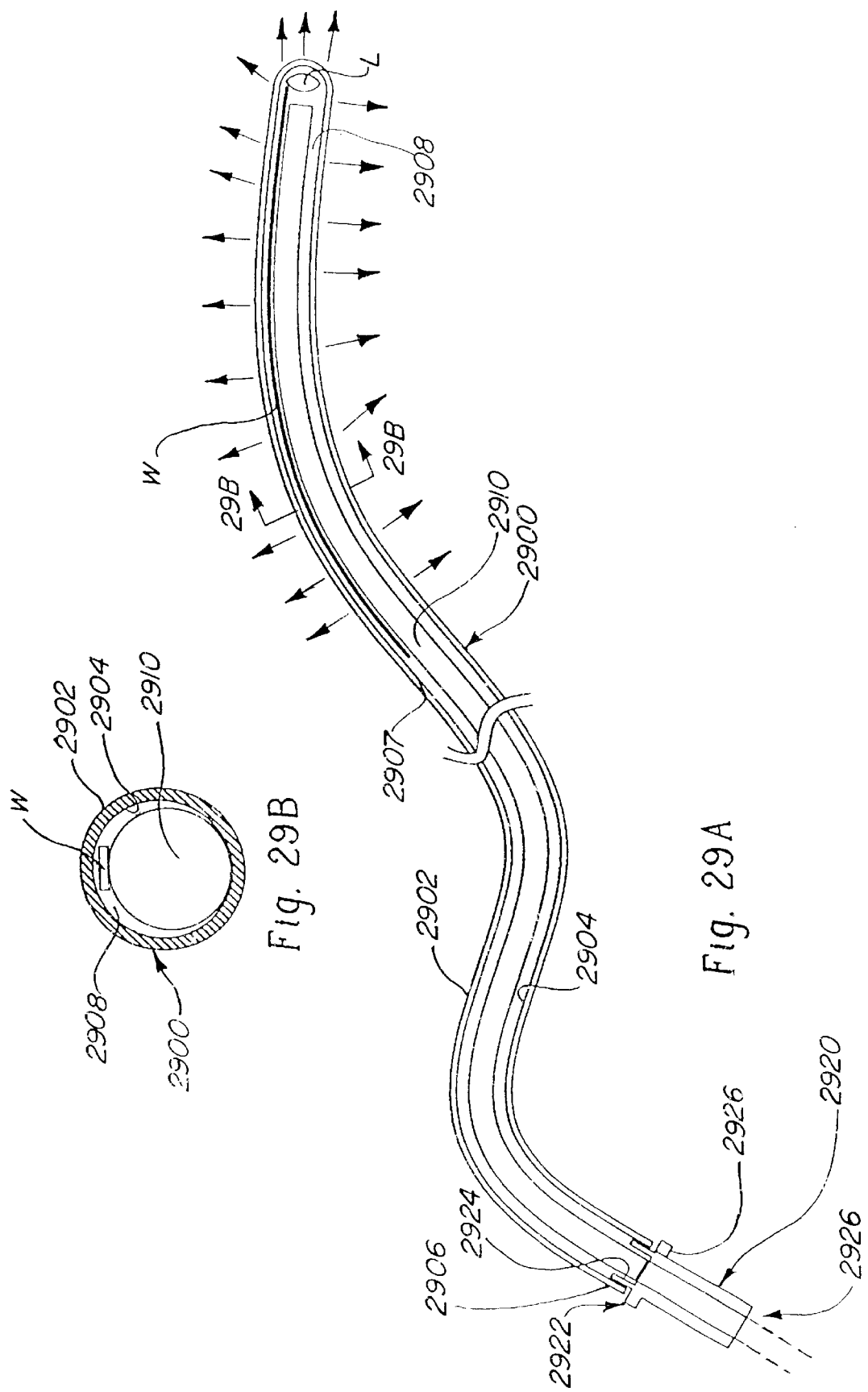

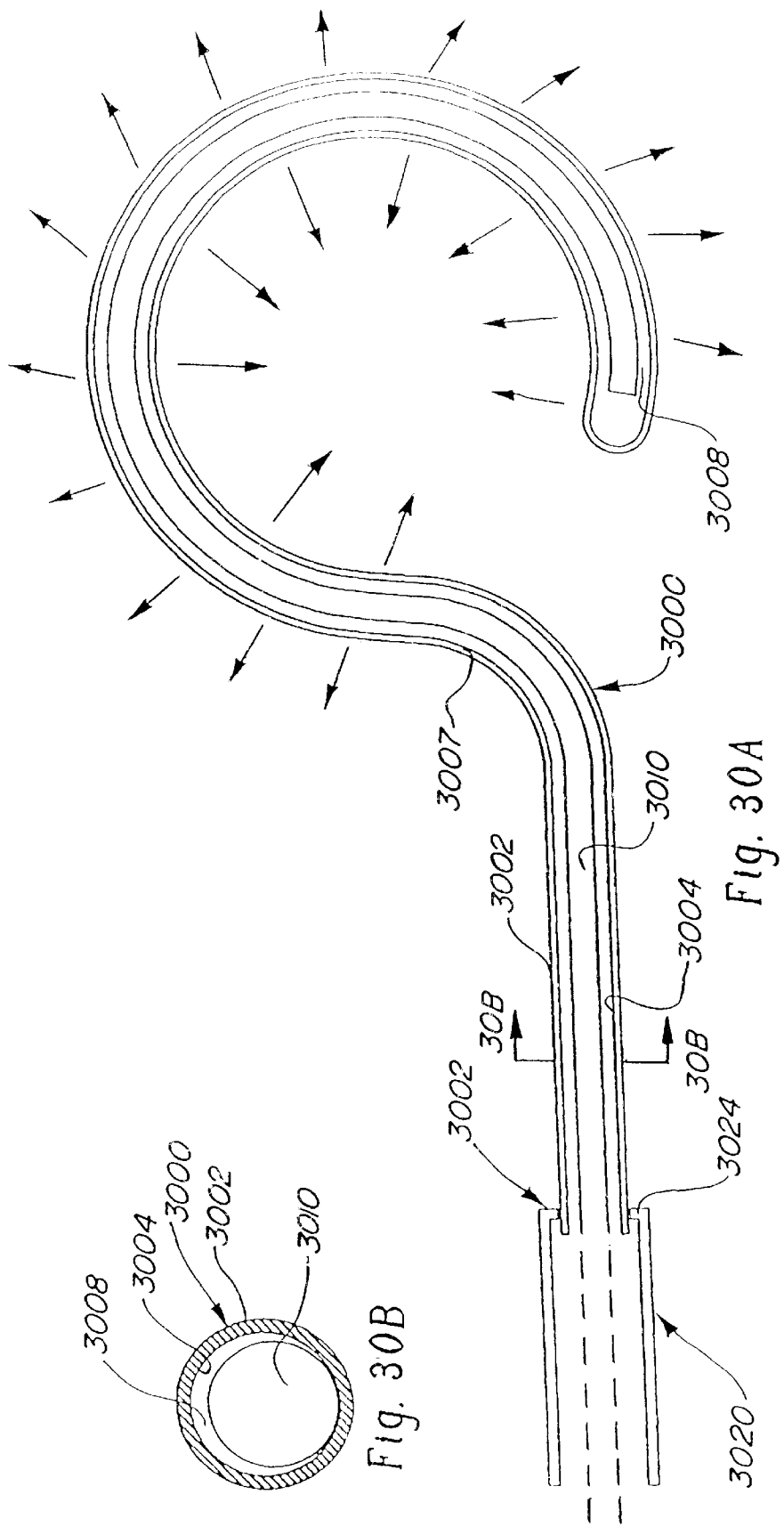

ILLUMINATED SURGICAL RETRACTOR

RELATED APPLICATIONS

The present application is a continuation of U.S. patent application Ser. No. 09/120,406 filed Jul. 22, 1998 now U.S. Pat. No. 6,185,356, which is a continuation-in-part of U.S. patent application Ser. No. 08/886,666 filed Jul. 2, 1997, which is a continuation-in-part of U.S. patent application Ser. No. 08/778,089, filed Jan. 2, 1997 (now U.S. Pat. No. 6,079,838), which is a divisional of U.S. patent application Ser. No. 08/495,176, filed Jun. 27, 1995 (now U.S. Pat. No. 5,613,751), U.S. patent application Ser. No. 08/778,180 filed Jan. 2, 1997 (now U.S. Pat. No. 5,921,652), which is a divisional of U.S. patent application Ser. No. 08/495,176 filed Jun. 27, 1995 now U.S. Pat. No. 5,613,751, and U.S. patent application Ser. No. 08/778,734, filed Jan. 2, 1997 (now U.S. Pat. No. 5,876,107), which is a divisional of U.S. patent application Ser. No. 08/495,176 filed Jun. 27, 1995 now U.S. Pat. No. 5,613,751. The contents of these applications are herein incorporated by reference.

FIELD OF INVENTION

The present invention relates generally to a protective cover, and more particularly to a protective cover for protecting a lighting device from direct contact with contaminants or components which may interfere with proper operation thereof.

BACKGROUND OF THE INVENTION

A common source of light for a light delivery system has been large stationary light generators, such as a 300 Watt Xenon light generator. A long light pipe or cable is used to connect the stationary light generator with a hand-held light delivery system. The light delivery system is suitably attached to an associated instrument or tool, or may form an integral part of the instrument or tool. However, the stationary light generators have some significant drawbacks. First, they are often costly. Institutions, such as hospitals, are reluctant to make such purchases, thus limiting the number of available light sources. Second, the stationary light generators are not portable, and thus limit the range of movement of the associated instrument or tool. Furthermore, the use of a stationary light generator prevents the associated instrument or tool from being a fully self-contained device. In this respect, it may be desirable to dispose of devices used in a surgical operation to prevent contamination.

It has also been recognized that typical light sources are relatively high-powered (e.g., 300 Watts). These high-powered sources of electrical energy provide the light that in turn is carried by a light distributor, such as a light pipe. If a contaminant (e.g., blood, dirt, etc.) or other component (e.g., adhesive pad) is in direct contact with the light distributor, it may interfere with the desired internal reflection of the light propagating through the light distributor. The contaminant or component changes the angle of reflection of light traveling through the light distributor. Accordingly, the optical energy is absorbed by the contaminant or component, and converted to heat. Consequently, the contaminant or component may quickly heat up to an undesirable temperature. Accordingly, there is a need to protect a lighting device from such interference, while maintaining its versatility.

The present invention overcomes these and other disadvantages of prior art lighting devices.

SUMMARY OF THE INVENTION

According to the present invention there is provided a protective cover or coating for shielding a light distributor from contact with contaminants or components associated with a lighting device.

An advantage of the present invention is the provision of a protective cover that prevents contaminants from interfering with the desired internal reflection of light propagating through a light distributor.

Another advantage of the present invention is the provision of a protective cover that prevents components for attaching accessory devices from interfering with the desired internal reflection of light propagating through a light distributor.

Still another advantage of the present invention is the provision of a protective cover that prevents contaminants and/or associated components from attenuating light traveling through a light distributor.

Yet another advantage of the present invention is the provision of a protective cover that prevents contaminants and/or associated components from heating up to an undesirable temperature level.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein:

FIG. 1 is an enlarged perspective view of a portion of the light emitter shown in FIG. 4A;

FIG. 2 is an enlarged transverse section through the light emitter shown in FIG. 1;

FIG. 3A is an enlarged plan view of a portion of a light emitter, showing one form of pattern of light extracting deformities on the light emitter;

FIGS. 3B–3D are enlarged schematic perspective views of a portion of a light emitter showing other forms of light extracting deformities formed in or on the light emitter;

FIG. 4A is a perspective view of a light delivery system, wherein the light delivery system is attachable to a suction/blower device;

FIG. 4B is a perspective view of the light delivery system shown in FIG. 4A, as attached to the suction/blower device;

FIG. 4C is a perspective view of an alternative embodiment of the attachment means for the light delivery system;

FIG. 5A is a perspective view of a suction/blower device having an integrated light delivery system;

FIG. 5B is an enlarged cross-sectional view taken along line 5B—5B of FIG. 5A;

FIG. 5C is an alternative embodiment of the cross-sectional view taken along line 5B—5B of FIG. 5A;

FIG. 10A is a perspective view of a stabilizer including an integrated light delivery system;

FIG. 10B is a side view of the stabilizer shown in FIG. 10A;

FIG. 13 is a perspective view of a multi-purpose lighting device including a light delivery system;

FIG. 14 is a sectional view of the multi-purpose lighting device taken along line 14—14 of FIG. 13;

FIG. 19A is a perspective view of a spring-formed "rope" lighting device;

FIG. 19B is a cross-sectional view of the lighting device taken along line 19—19 of FIG. 19A;

FIG. 20A is a perspective view of a smoke evacuation tube having an integrated light delivery system;

FIG. 20B is a cross-sectional view of the smoke evacuation tube taken along line 20—20 of FIG. 20A;

FIG. 21A is a perspective view of a suction tube having an integrated light delivery system;

FIG. 21B is a cross-sectional view of the suction tube taken along line 21—21 of FIG. 21A;

FIG. 22A is a perspective view of a suction tube having an attachable light delivery system;

FIG. 22B is a cross-sectional view of the suction tube taken along line 22—22 of FIG. 22A;

FIG. 25A is a perspective view of a protective cover applied to a light distributor, in accordance with another embodiment of the present invention;

FIG. 25B is a cross-sectional view of the protective cover, taken along line 25B—25B of FIG. 25A;

FIG. 25C is an end view of the protective cover shown in FIG. 25A;

FIG. 25D is a cross-sectional view of the protective cover, taken along line 25D—25D of FIG. 25C;

FIG. 26A is a perspective view of a protective cover applied to a light distributor, in accordance with yet another embodiment of the present invention;

FIG. 26B is a cross-sectional view of the protective cover, taken along line 26B—26B of FIG. 26A;

FIG. 26C is an end view of the protective cover shown in FIG. 26A;

FIG. 26D is a cross-sectional view of the protective cover, taken along line 26D—26D of FIG. 26;

FIG. 27A is a cut-away view of a protective cover according to another embodiment of the present invention as applied to a light rod;

FIG. 27B is a cross-sectional view of the protective cover taken along line 27B—27B of FIG. 27A;

FIG. 28A is a cut-away view of a protective cover as applied to a light rod with attached retractor blade;

FIG. 28B is a cross-sectional view of the protective cover taken along line 28B—28B of FIG. 28A;

FIG. 29A is a cut-away view of a protective cover according to another embodiment of the present invention as applied to a rope light;

FIG. 29B is a cross-sectional view of the protective cover taken along line 29B—29B of FIG. 29A;

FIG. 30A is a cut-away view of a protective cover according to another embodiment of the present invention as applied to a ring light;

FIG. 30B is a cross-sectional view of the protective cover taken along line 30B—30B of FIG. 30A;

DETAILED DESCRIPTION OF THE PREFERRED EMBODIMENT

Figure 6:
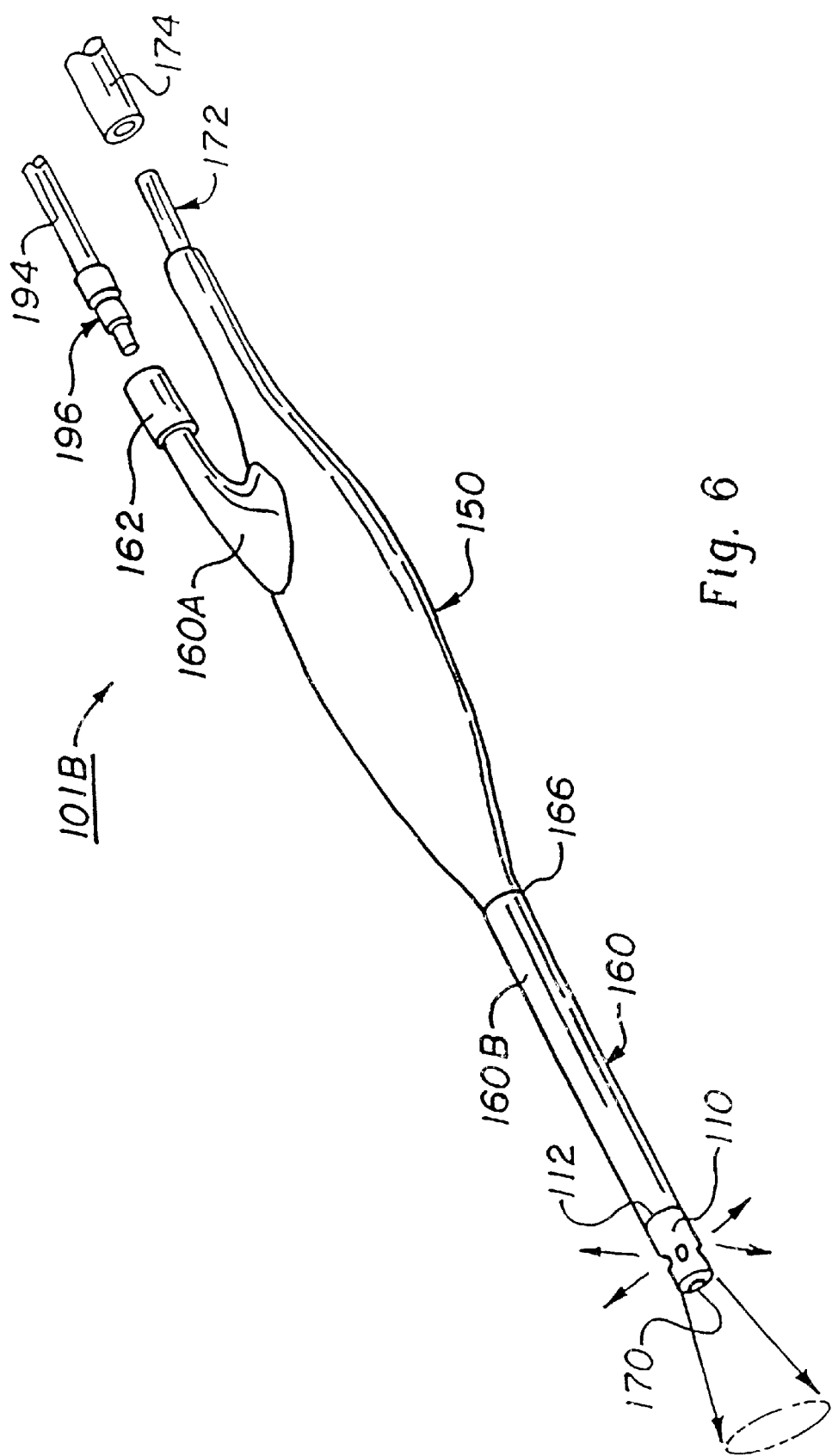
FIG. 6 is a perspective view of another type of suction/blower device having an integrated light delivery system.

Referring now to the drawings wherein the showings are for the purposes of illustrating a preferred embodiment of the invention only and not for purposes of limiting same, FIGS. 4A and 4B illustrate a suction/blower device 100 having an externally mounted light delivery system 2. FIG. 4A shows a light delivery system 2 detached from suction/blower device 100, while FIG. 4B shows light delivery system 2 attached to suction/blower device 100. It should be appreciated that device 100 can take many forms including a surgical instrument or a conventional hand tool, as will be illustrated below.

Light delivery system 2 is generally comprised of a light emitter 10, a light distributor 60, and an attachment means 80. Light emitter 10 focuses light of varying intensity in a predetermined direction or pattern. As a result, an associated viewing field is illuminated with a predetermined light characteristic. Light distributor 60 (e.g., optic light pipe) transmits light from a light source 90 to light emitter 10. Attachment means 80 provides a support structure for coupling light delivery system 2 to device 100. In this regard, attachment means 80 may include tabs, hooks or the like.

Light emitter 10 is comprised of a transparent or translucent light emitting material of any suitable type, including acrylic, polycarbonate, glass, epoxy, resins or the like. Emitter 10 may be substantially flat, suitably curved, may be formed of single or multiple layers, and may have different thicknesses and shapes. Moreover, emitter 10 may be flexible, or rigid, and may be made out of a variety of compounds. It should also be appreciated that emitter 10 may be hollow, filled with liquid, air, or be solid, and may have holes or ridges formed therein.

Means for directing light in desired directions and patterns, and providing various light intensity levels will now be described with reference to FIGS. 1 and 2, which show a section B of light emitter 10. Light extracting formations including deformities, disruptions, coatings, patterns or lenses, may be provided on one or more selected light surface areas 20 on one or more sides 21 or edges 23 of emitter 10. As used herein, the term light extracting formation is to mean any change in the shape or geometry of the surface and/or coating or surface treatment that causes a portion of the light to be emitted. FIG. 3A schematically shows one such light surface area 20 on which a pattern of light extracting deformities or disruptions 22 is provided. The pattern of light extracting deformities or disruptions 22 shown in FIG. 3A includes a variable pattern which breaks up the light rays such that the internal angle of reflection of a portion of the light rays will be great enough to cause the light rays either to be emitted out of emitter 10 through the side or sides on which the light extracting deformities or disruptions 22 are provided or reflected back through the emitter 10 and emitted out the other side thereof.

Light extracting formations can be produced in a variety of manners, for example, by providing a painted pattern, an etched pattern, a machined pattern, a printed pattern, a hot stamped pattern, a molded pattern, a curved surface (i.e., lens), a diffraction grating, a prismatic surface or the like on selected light surface areas 20 of emitter 10. An ink or printed pattern may be applied for example by pad printing, silk screening, ink jet, heat transfer film process or the like. The deformities or disruptions may also be printed on a sheet or film which is used to apply the deformities or disruptions to light surface area 20. This sheet or film may become a permanent part of emitter 10 for example by attaching or otherwise positioning the sheet or film against one or both sides of the emitter light surface area similar to the sheet or film 24 shown in FIGS. 1 and 2 in order to produce a desired effect.

By varying the density, opaqueness or translucence, shape, depth, color, area, index of refraction, diffraction grating, or type of light extracting formations, the light output of emitter 10 can be controlled. The light extracting formations may be used to control the direction and/or percent of light emitted from any area of emitter 10. For instance, less and/or smaller size deformities 22 may be placed on emitter 10 in areas where less light output is wanted. Conversely, a greater percentage of and/or larger deformities 22 may be placed on emitter 10 in areas where greater light output is desired.

Varying the percentages and/or size of deformities 22 in different areas of emitter 10 is necessary in order to provide a uniform light output distribution. For example, the amount of light traveling through light emitter 10 will ordinarily be greater in areas closer to the light source than in other areas further removed from the light source. A pattern of light extracting deformities 22 may be used to adjust the light variances within the emitter, for example, by providing a denser concentration of light extracting deformities with increased distance from the light source thereby resulting in a more uniform light output distribution from light emitter 10. The deformities 22 may also be used to control the output ray angle distribution of the emitted light to suit a particular application.

It should be appreciated that other light extracting formations are suitably provided in addition to or in lieu of the patterns of light extracting deformities 22 shown in FIG. 3A. As indicated above, other light extracting formations include lenses, prismatic surfaces, depressions or raised surfaces of various shapes using more complex shapes in a mold pattern may be molded, etched, stamped, thermoformed, hot stamped or the like into or on one or more surface areas (e.g., sides and edges) of the light emitter. Lenses (e.g., pillow lenses) can be used to provide diffuse light (by spreading light rays) and directional light (by focusing light rays). FIGS. 3B and 3C show areas 26 on which prismatic surfaces 28 or depressions 30 are formed in the emitter surface area, whereas FIG. 3D shows prismatic or other reflective or refractive surfaces 32 formed on the exterior of the emitter surface area. The prismatic surfaces, depressions or raised surfaces will cause a portion of the light rays contacted thereby to be emitted from the light emitter. Also, the angles of the prisms, depressions or other surfaces may be varied to direct the light in different directions to produce a desired light output distribution or effect, or to project a spot image or pattern of light to a specific area or region. Moreover, the reflective or refractive surfaces may have shapes or a pattern with no specific angles to reduce moire or other interference effects. In addition, the light rays emitted from the emitter may provide generally shadowless or homogenous light. In this regard, the emitter may simultaneously illuminate a 3-D object from a plurality of sides.

As best seen in the cross-sectional view of FIG. 2, a back reflector 34 (including trans reflectors) may be attached or positioned against one side of the panel member 14 of FIG. 1 using a suitable adhesive 36 or other method in order to improve light output efficiency of light emitter 10 by reflecting the light emitted from that side back through the panel for emission through the opposite side. Additionally, a pattern of light extracting deformities 22, 28, 30 and/or 32 may be provided on one or both sides of the light emitter in order to change the path of the light so that the internal critical angle is exceeded and a portion of the light is emitted from one or both sides of the light emitter. Moreover, a transparent film, sheet or plate member 24 may be attached or positioned against the side or sides of the emitter from which light is emitted using a suitable adhesive 36 or other method in order to produce a desired effect.

Member 24 may be used to further improve the uniformity of the light output distribution. For example, member 24 may be a colored film, a diffuser, or a label or display, a portion of which may be a transparent overlay that may be colored and/or have text or an image thereon.

If adhesive 36 is used to adhere the back reflector 34 and/or film 24 to the emitter, the adhesive is preferably applied only along the side edges of the emitter, and if desired the end edge opposite light transition areas, but not over the entire surface area or areas of the emitter because of the difficulty in consistently applying a uniform coating of adhesive to the panel. Also, the adhesive changes the internal critical angle of the light in a less controllable manner than the air gaps 40 (see FIG. 2) which are formed between the respective surfaces of the emitter and the back reflector 34 and/or member 24 when only adhered along the peripheral edges. Additionally, longer emitters are achievable when air gaps 40 are used. If adhesive were to be used over the entire surface, the pattern of deformities could be adjusted to account for the additional attenuation in the light caused by the adhesive.

The light emitter disclosed herein may be used for a great many different applications including for example LCD back lighting or lighting in general, decorative and display lighting, automotive lighting, dental lighting, phototherapy, photodynamic therapy, or other medical lighting, membrane switch lighting, and sporting goods and apparel lighting or the like. Also the emitter may be formed such that the deformities are transparent without a back reflector. This allows the emitter to be used such that the application is viewed through the transparent emitter.

The light that is transmitted by light distributor 60 to light emitter 10 may be emitted along the entire length of light emitter 10 or from one or more light output areas along the length of the panel as desired to produce a desired light output distribution to fit a particular application.

Light distributor 60 is a formed light conduit adapted to propagate light therethrough via internal reflection. In the embodiment illustrated in FIG. 4A and 4B, light distributor 60 takes the form of an optic light pipe. Light distributor 60 includes an interface 64 and a connecting member 62. Interface 64 interfaces light distributor 60 with light emitter 10. Connecting member 62 facilitates connection of light distributor 60 with light source 90 (described below). It should be appreciated that light distributor 60, light emitter 64, and light source 90 may be formed as one unitary member without interface 64 and connecting member 62.

Light source 90 may take many forms as will be discussed below. In the embodiment of the present invention shown in FIGS. 4A and 4B, light source 90 is generally comprised of a generator 92 and a cable 94. Generator 92 may be, for example, a 300 Watt Xenon light source. Cable 94 includes a connecting member 96, which mates with connecting member 62 of light distributor 60.

It should be appreciated that light source 90 illustrated in FIGS. 4A and 4B is shown solely for the purpose of illustrating an embodiment of the present invention. In this respect, light source 90 may also be of other suitable types including, an arc lamp, an incandescent bulb (which also may be colored, filtered or painted), a lens end bulb, a line light, a halogen lamp, a light emitting diode (LED), a chip from an LED, a neon bulb, a fluorescent tube, a laser or laser diode, or any other suitable light source. For example, light source 90 may take the form of any of the types disclosed in U.S. Pat. Nos. 4,897,771 and 5,005,108, assigned to the same assignee as the present application, the entire disclosures of which are incorporated herein by reference. Additionally, the light source may be a multiple colored LED, or a combination of multiple colored radiation sources in order to provide a desired colored or white light output distribution. For example, a plurality of colored lights such as LEDs of different colors (red, blue, green) or a single LED emitting a selected spectrum may be employed to create white light or any other colored light output distribution by varying the intensities of each individual colored light.

Attachment means 80 is suitably molded as an integral part of light distributor 60 (FIG. 4A), attaches to both the light distributor and the associated device (FIG. 4C), or forms a part of device 100. In the embodiment shown in FIG. 4A and 4B, attachment means 80 is fixed to light distributor 60, wherein gripping means 84 are provided for attaching light delivery system 2 to device 100. Attachment means 80 allows light delivery system 2 to be easily and conveniently attached to and detached from suction/blower device 100. As a result, light delivery system 2 is easily replaced where sterilization is required.

In the embodiment shown in FIG. 4C, one form of attachment means 80 includes engagement means 82 and 84 for fixing light delivery system 2 to a device. In this respect, engagement means 82 are engageable with light distributor 60, while engagement means 84 are engageable with a portion of the device. It should be appreciated that engagement means 82 and/or engagement means 84 are suitably integral with light distributor 60 and the device, respectively. However, in the case where convenient replacement of light delivery system 2 is desired (e.g., when sterilization is required) engagement means 82 and/or engagement means 84 will preferably provide for convenient removal of light delivery system 2 from the device. For instance, in the embodiment shown in FIGS. 4A and 4B, engagement means 84 takes the form of a clamp, which allows for simple attachment and detachment of light delivery system 2 from device 100. It should be appreciated that engagement means 82 and 84 may take the form of other suitable fastening members including cables, snaps, clips, tabs, adhesives, and the like.

Device 100 includes a tube 70 having a tip portion 76. Tip portion 76 is comprised of a plurality of openings 78, which are in communication with tube 70. Light emitter 10 is suitably dimensioned to receive tip portion 76, when light delivery system 2 is attached to device 100 (FIG. 4B). It should be noted that light emitter 10 is suitably formed to provide diffuse light in directions transverse to the longitudinal axis of device tip portion 76, and to provide direct light in a direction generally parallel to the longitudinal axis of tip portion 76. As indicated above, the direct light provides maximum illumination on the material being suctioned or blown. At the same time, the diffuse light provides sufficient, but not over bright, illumination of the area surrounding the material being suctioned or blown. As a result, the user's vision of the material being suctioned or blown is not impaired.

Other embodiments of the present invention will now be described with reference to FIGS. 5–22, which illustrate a variety of different surgical instruments and hand tools which are used in conjunction with the light delivery system of the present invention.

Referring now to FIG. 5A, there is shown a suction/blower device 101A. Device 101A is a surgical instrument typically used to remove material (e.g., fluid or tissue) from a surgeons field of view. In this respect, device 101A suctions or blows the obscuring material. Device 101A is generally comprised of a light emitter 110, a light distributor 160 and air passageway(s) 170. Light distributor 160 includes a connecting member 162 dimensioned to receive a mating connecting member 196 from cable 194. Cable 194 is connected to a light source (not shown).

It is important to note that light distributor 160 not only carries light to light emitter 110, but also provides a support structure for suction/blower device 101A. In this respect, light distributor 160 includes a light distribution member 161, which is constructed of a rigid material and formed into a suitable shape for a user to conveniently hold device 101A. Light distribution member 161 transmits light and defines passageway(s) 170. Passageway(s) 170 are generally tubular hollow channels formed along the length of light distributor 160. FIGS. 5B and 5C illustrate two different embodiments for light distributor 160. Passageway(s) 170 provides a conduit for air, or other gas or fluid. Light distributor 160 also includes an outer layer 163. Outer layer 163 may take the form of a heat-shrinked film, coating or tubing. Outer layer 163 provides a protective layer for light distribution member 161. Similarly, an inner layer (not shown) may line the inner surface of light distribution member 161. The outer and inner layers protect the internal light propagation from impairment (e.g., blood or other materials that can cause light loss). It should be appreciated that light distributor 160 may be constructed of a plurality of walls of varying thickness. The walls may take the form of a film, coating or tubing. Moreover, the film, coating or tubing may extend along the full length of light distributor 160, or only along a portion thereof.

A connector 172 is provided to receive a mating connector from a hose 174. Hose 174 is connected to a vacuum generating means (not shown), where device 101A is used for suction, or is connected to a blower means (not shown), where device 101A is used for blowing. Light emitter 110 is located at the tip end of device 101A, and surrounds passageway(s) 170. Light emitter 110 is suitably formed to provide diffuse light in directions transverse to the longitudinal axis of device 101A, and to provide direct light in a direction generally parallel to the longitudinal axis of device 101A. In this way, the direct light provides maximum illumination on the material being suctioned or blown. At the same time, the diffuse light provides sufficient, but not over bright, illumination of the area surrounding the material being suctioned or blown. As a result, the user's vision of the material being suctioned or blown is not impaired.

It should be appreciated that light distributor 160 and light emitter 110 form an integral part of the suction/blowing device 101A, and thus eliminate the need for an external lighting device mounted to the suction/blowing device, a lighting device mounted elsewhere in an operating room, or a hand held lighting device.

FIG. 6 illustrates an alternative embodiment of suction/blower device 101A. Suction/blower device 101B is similar in many respects to suction/blower device 101A; however, light emitter 110 and light distributor 160 are disposable in this embodiment. In this respect, suction/blower 101B is generally comprised of a light emitter 110, a rigid body member 150, a light distributor 160 having a fixed portion 160A and a detachable portion 160B, and a tube 170. Body member 150 is constructed of a rigid material (e.g., plastic) and formed into a suitable shape for a user to conveniently hold device 101B. Body member 150 surrounds fixed portion 160A of light distributor 160. Fixed portion 160A includes a connecting member 162. Fixed portion 160A and detachable portion 160B are connected at interface 166. A hollow channel is formed along the length of portions 160A and 160B to provide tube 170. Light emitter 110 is optionally detachable from light distributor 160 at interface 166.

It should be appreciated that suction/blower device 101B has the advantage of having a detachable light emitter 110 and light distributor 160. This allows for convenient replacement of the portions of device 101B which may require sterilization. As a result, only an inexpensive and small portion of device 101B is disposed, thus saving the expense of replacing the entire suction/blower device 101B.

Figure 7:
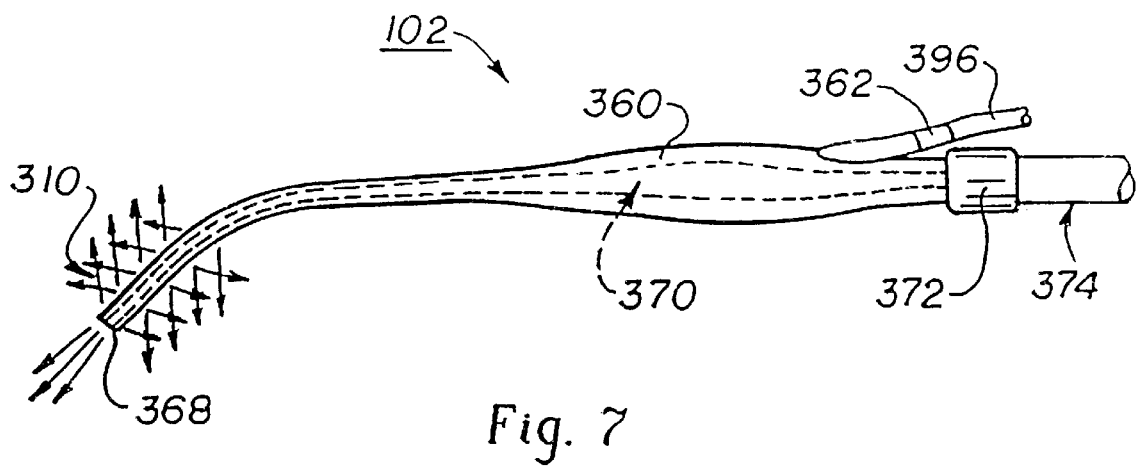
FIG. 7 is a perspective view of yet another type of suction/blower device having an integrated light delivery system.

FIG. 7 illustrates another suction/blower device 102. Device 102 is generally comprised of a light emitter 310, a light distributor 360 and a tube 370. Light distributor 360 has a connecting member 362 dimensioned to receive a mating connecting member 396 from cable 394. Cable 394 is connected to a light source (not shown). It is important to note that light distributor 360 not only carries light to light emitter 310, but also provides a support structure for suction/blower device 102. In this respect, light distributor 360 is constructed of a rigid material and formed into a suitable shape for a user to conveniently hold device 102. In addition, a hollow channel is formed along the length of light distributor 360 to provide tube 370. Light distributor 360 is preferably formed of an inexpensive plastic material. Tube 370 includes a connector 372, dimensioned to receive a mating connector from a hose 374. Hose 374 is connected to a vacuum generating means (not shown), where device 102 is used for suction, or is connected to a blower means (not shown), where device 102 is used for blowing. Light emitter 310 is located at tip 368 of light distributor 360, and surrounds tube 370. Light emitter 310 is suitably formed to provide diffuse light in directions transverse to the longitudinal axis of tip 368, and to provide direct light in a direction generally parallel to the longitudinal axis of tip 368. In this way, the direct light provides maximum illumination on the material being suctioned or blown. At the same time, the diffuse light provides sufficient, but not over bright, illumination of the area surrounding the material being suctioned or blown. As a result, the user's vision of the material being suctioned or blown is not impaired.

It should be appreciated that light distributor 360 is easily and conveniently attached to and detached from cable 394 and hose 374. As a result, light delivery system 202 is easily replaced where sterilization is required.

Figure 8:
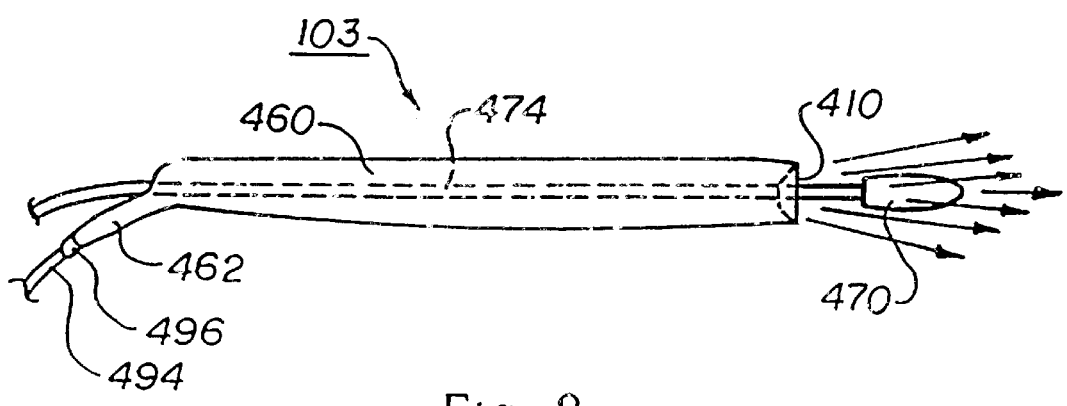
FIG. 8 is a perspective view of an electrosurgical pencil including the light delivery system of the present invention.

FIG. 8 illustrates an electrosurgical pencil device 103. Electrosurgical pencil device 103 is used to destroy tissue by burning the tissue with a cauterizing tip. Device 103 is generally comprised of a light emitter 410, a light distributor 460 and a cauterizing tip 470. Light distributor 460 has a connecting member 462 dimensioned to receive a mating connecting member 496 from a cable 494. Cable 494 is connected to a light source (not shown). It is important to note that light distributor 460 not only conducts light to light emitter 410, but also provides a support structure for device 103. In this respect, light distributor 460 is constructed of a rigid material and formed into a suitable shape for a user to conveniently hold device 103. In addition, a channel is formed along the length of light distributor 460 to provide a passageway for electrical conductor 474. Electrical conductor 474 connects to cauterizing tip 470, to provide power thereto. Light emitter 410 is suitably formed to provide diffuse light in directions transverse to the longitudinal axis of tip 470, and to provide direct light in a direction generally parallel to the longitudinal axis of tip 470. In this way, the direct light provides maximum illumination on the material being cauterized. At the same time, the diffuse light provides sufficient, but not over bright, illumination of the area surrounding the material being cauterized. As a result, the user's vision of the material being cauterized is not impaired.

Figure 9A:
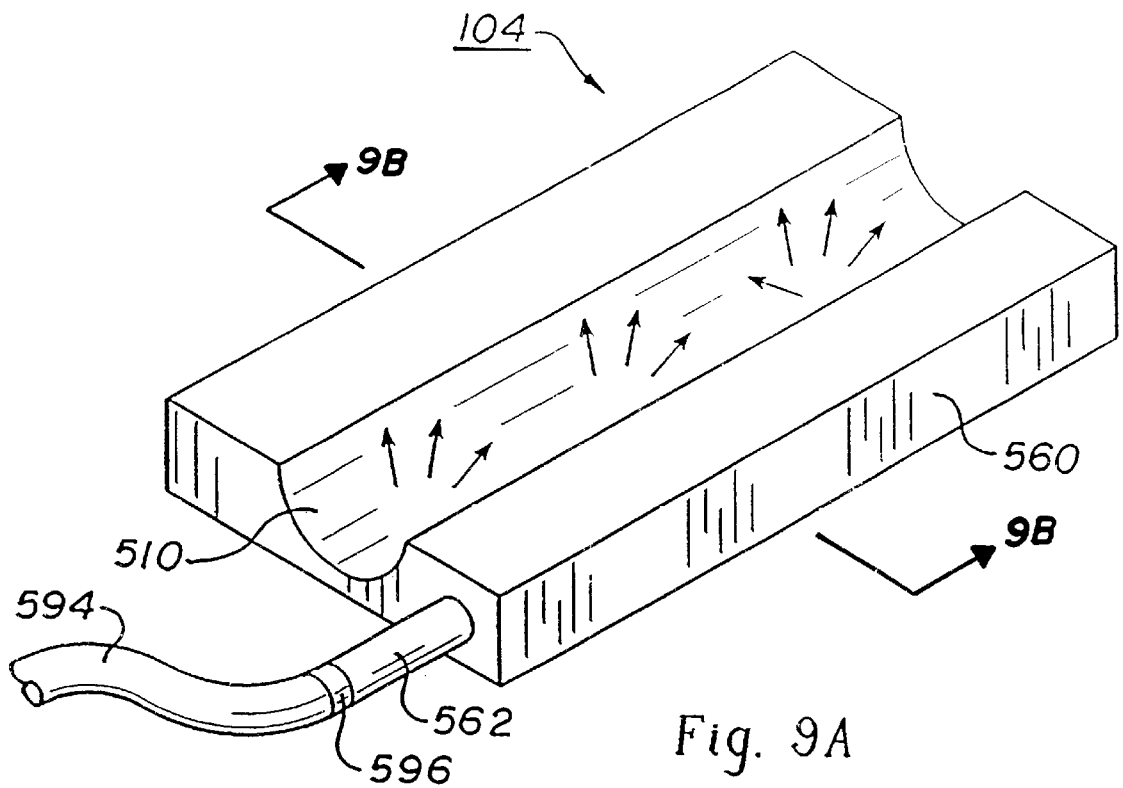
FIG. 9A is a perspective view of a transillumination tray including the light delivery system of the present invention.
Figure 9B:
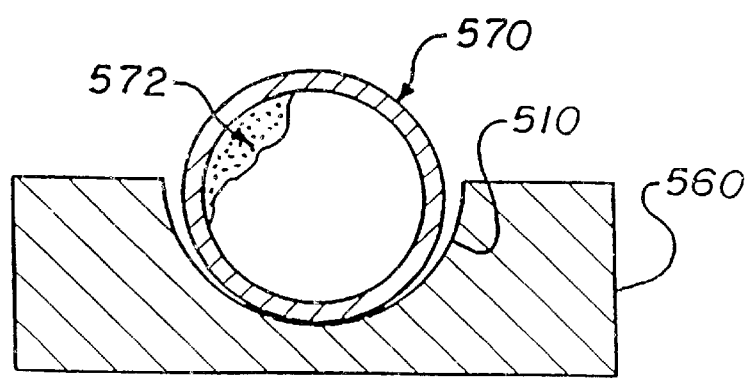
FIG. 9B is a cross-sectional view taken along line 9B—9B of FIG. 9A, with a vein/artery located in the transillumination tray.

Referring now to FIG. 9A, there is shown a transillumination tray 104 for illuminating a bodily structure (e.g., vein, artery, finger, or small organ). Tray 104 is generally comprised of a light distributor 560 and a light emitter 510. Light distributor 560 includes a connecting member 562 dimensioned to receive a mating connecting member 596 from a cable 594. Cable 594 is connected to a light source (not shown). It is important to note that light distributor 560 not only conducts light to light emitter 510, but also provides a support base for tray 104. In this respect, light distributor 560 is constructed of a rigid material and formed into a suitable shape for receiving a generally U-shaped light emitter 510. Light emitter 510 is shaped to receive a bodily structure, and thoroughly illuminate it. In this respect, light is emitted in all directions from the surface of light emitter 510. FIG. 9B illustrates a cross-sectional view of tray 104 with a vein/artery 570 located on tray 104 for examination. Light emitter 510 illuminates an obstruction 572 in vein/artery 570.

FIGS. 10A and 10B show a stabilizer device 105 including the light delivery system of the present invention. Stabilizer device 105 is generally comprised of light emitters 610A, 610B and 610C, and a light distributor 660. Light distributor 660 includes a central portion 670, arm portions 672, and connecting member 662. Connecting member 662 is dimensioned to receive a mating connecting member 696 from a cable 694 (such as a light pipe). Cable 694 is connected to a light source (not shown). It is important to note that light distributor 660 not only carries light to light emitters 610A, 610B and 610C, but also provides a support structure for stabilizer device 105. In this respect, light distributor 660 is constructed of a rigid material and formed into a suitable shape for a user to conveniently hold device 102. Light emitters 610A, 610B and 610C provide different lighting conditions. In this respect, light emitter 610A may includes a lens 611 for providing direct focused light on incision work area I. Light emitter 610B is formed along the periphery defined by central portion 670 and arm portions 672. Light emitter 610B provides indirect diffuse light for incision work area I. Light emitter 610C is formed along the lower edge (i.e., bottom) of central portion 670 and arm portions 672. Light emitter 610C may provide indirect diffuse light or glowing light for transillumination of a bodily structure.

It should be appreciated that in an alternative embodiment, stabilizer device 105 may be suitably arranged to attach (e.g., using a clip or other attachment means) to a metal stabilizer having the same general shape as stabilizer device 105. In this regard, the strength of the material forming stabilizer device 105 may not sufficient for a particular application. Accordingly, the metal stabilizer provides the desired strength.

Figure 11:
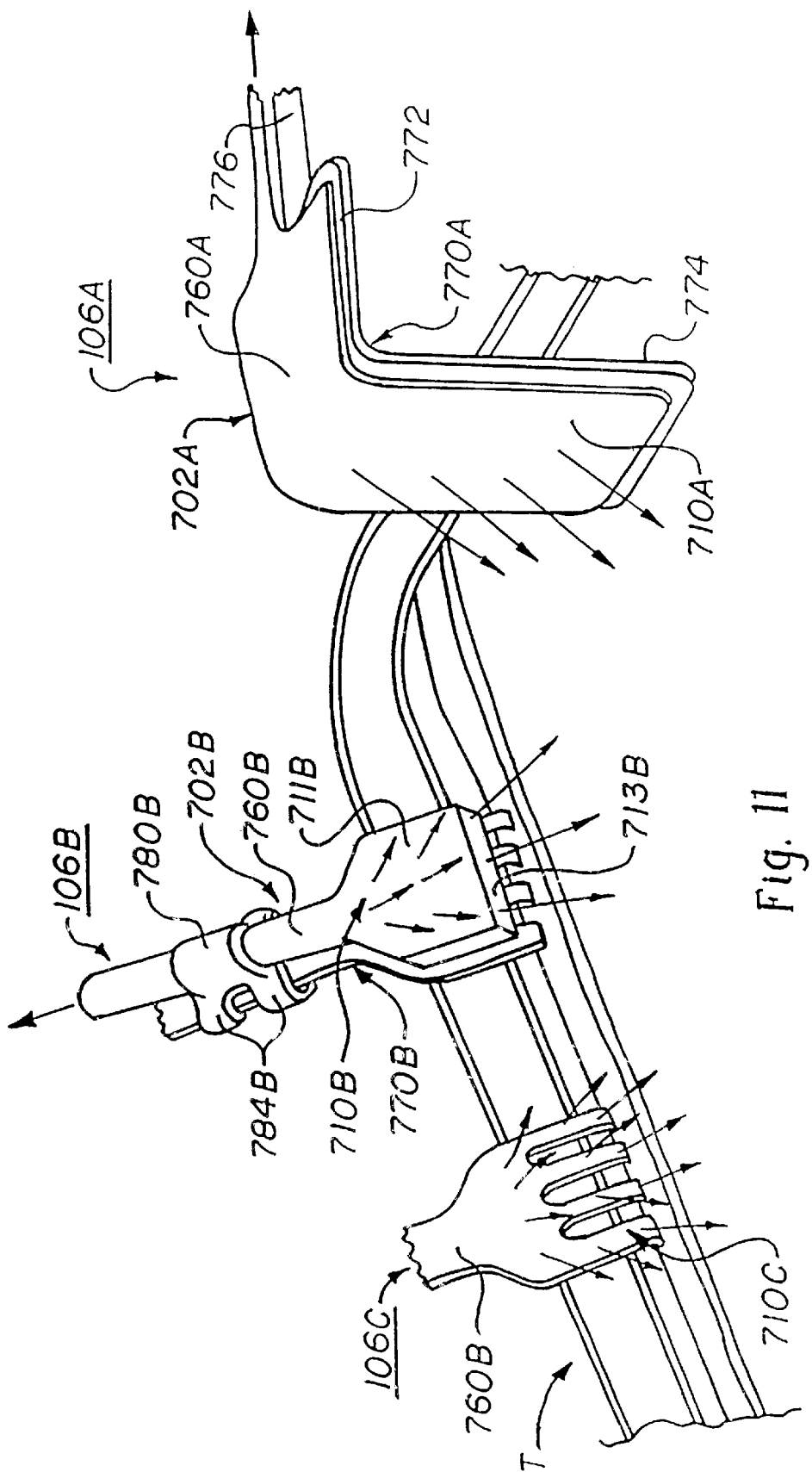
FIG. 11 is a perspective view of a plurality of retractors including a light delivery system.

Referring now to FIG. 11, there is shown retractor devices 106A, 106B and 106C for retracting body structure T (which may include, bodily tissue, bone, organs or the like). Retractor device 106A is comprised of a retractor member 770A and a light delivery system 702A. Retractor member 770A includes a horizontal portion 772, a vertical portion 774, and a support member 776. Support member 776 is arranged between horizontal portion 772 and a rigid mount (not shown). Light delivery system 702A is mounted to the front face of vertical portion 774, and includes a light distributor 760A and a light emitter 710A. Light distributor 760A bends to follow the general shape of retractor member 770A, and receives light from a light source (not shown). A suitable adhesive may be used to attach light delivery system 702A to vertical portion 774. Light emitter 710A provides diffuse or directional light into the work area.

Retractor device 106B is generally comprised of a retractor member 770B and a light delivery system 702B. Retractor member 770B is a rake retractor having a plurality of prongs. Light delivery system 702B includes an attachment member 780B, light distributor 760B, and light emitter 710B. Attachment member 780B has engagement means 784B for attaching light delivery system 702B to retractor member 770B. Light distributor 760B receives light from a light source (not shown). Light emitter 710B includes a top portion 711B and a side portion 713B. Light emitter 710B provides diffuse or directional light into the work area.

Retractor device 106C is a rake retractor formed of a translucent material (e.g., plastic). Retractor device 106C includes light distributor 760B and light emitter 710C. The light distributor 760B and light emitter 710C form the structural member of retractor device 106C.

Figure 12:
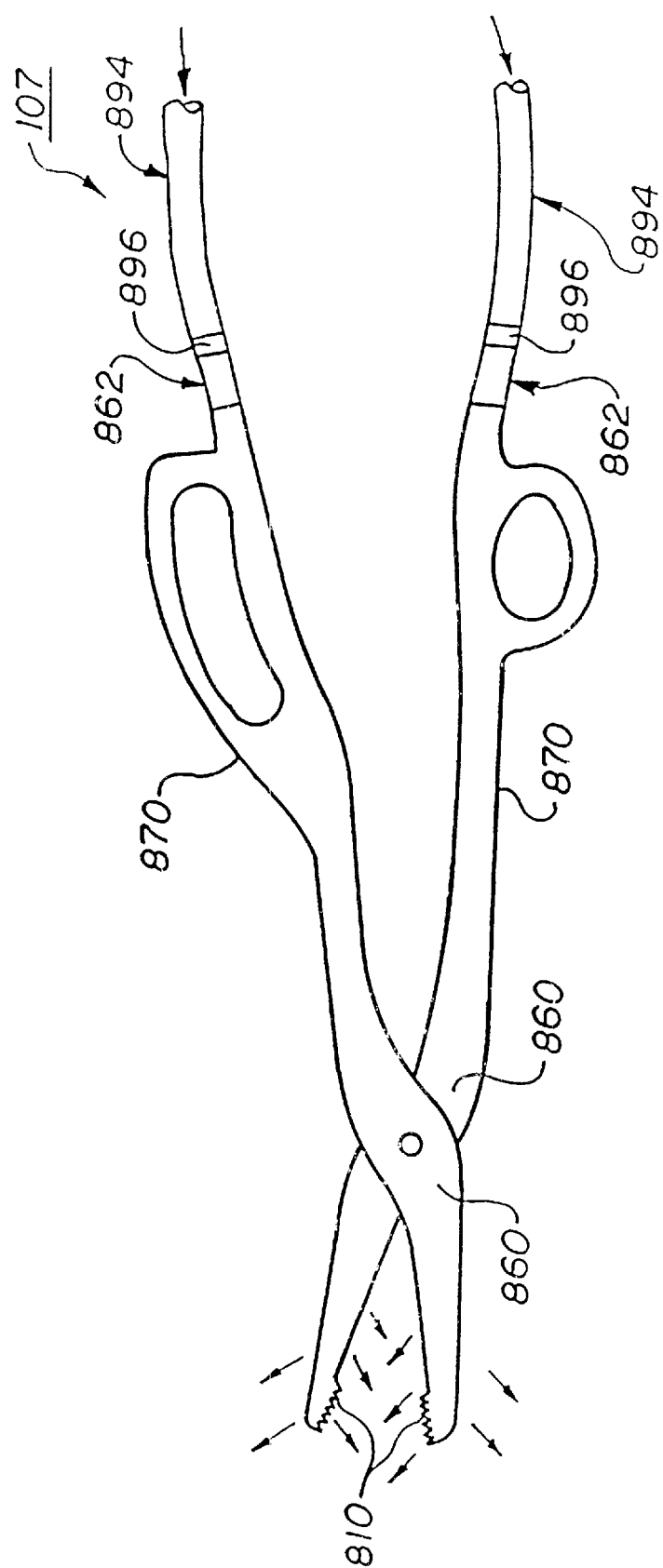
FIG. 12 is a top view of a forceps including an integrated light delivery system.
Figure 15:
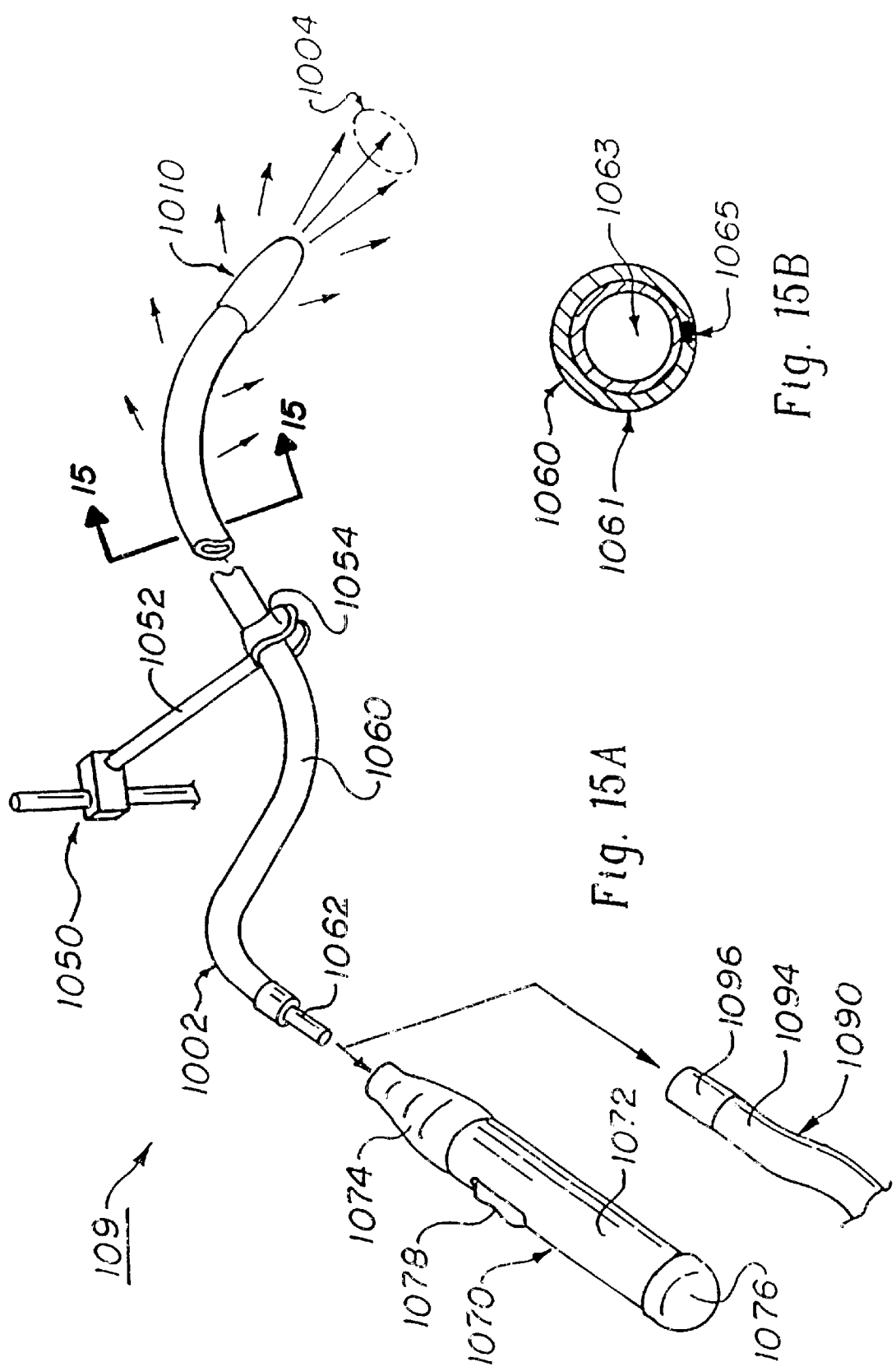
FIG. 15A is a perspective view of a lighting device including a light delivery system.
FIG. 15B is a sectional view of the lighting device taken along line 15—15 of FIG. 15A.
Figure 16:
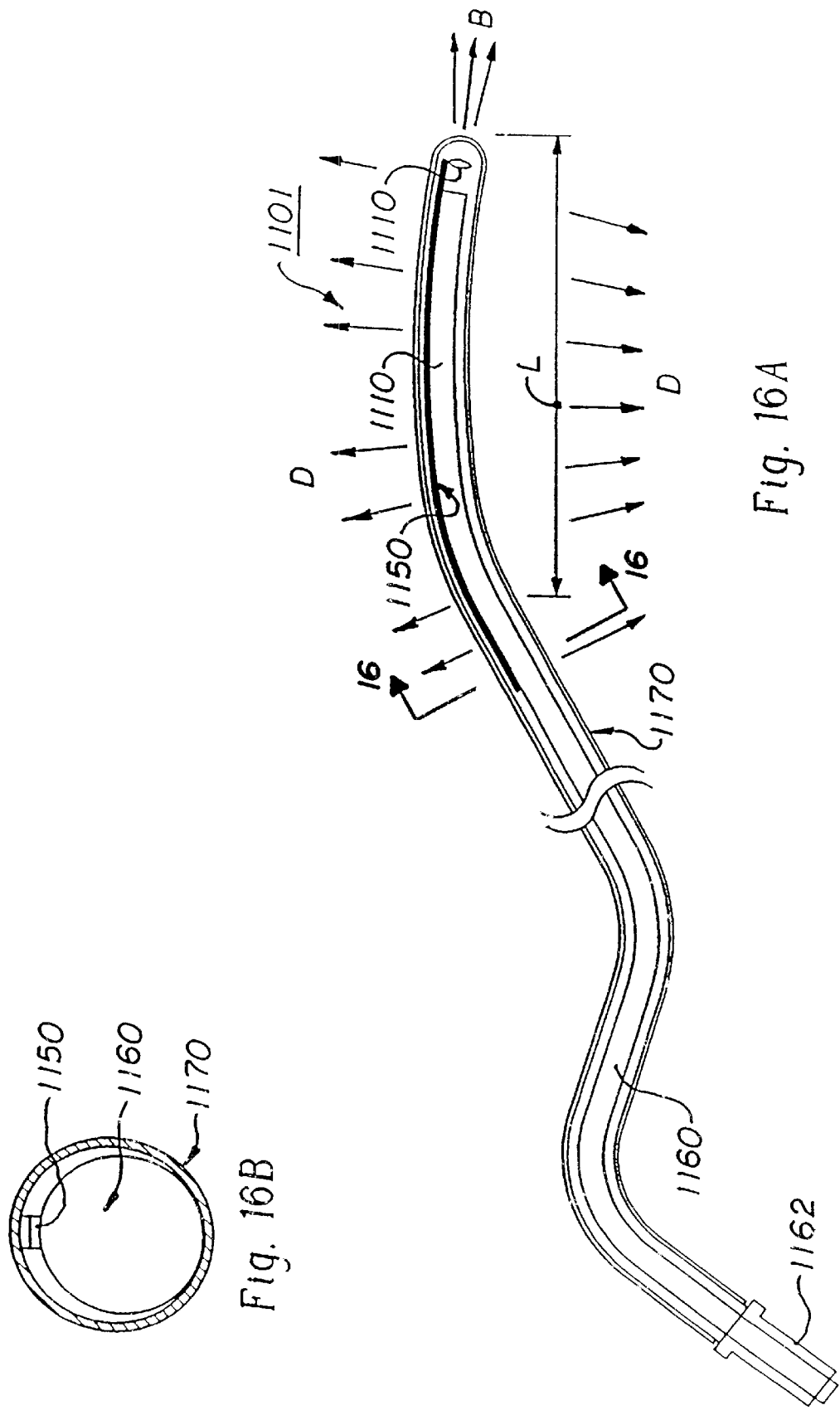
FIG. 16A is a perspective view of a "rope" lighting device.
FIG. 16B is a cross-sectional view of the lighting device taken along line 16—16 of FIG. 16A.

Referring now to FIG. 12, there is shown an illuminated forceps 107 having an integrated light delivery system. Forceps 107 is generally comprised of light distributors 860 and light emitters 810. Each light distributor 860 includes a pair of arms 870 and a pair of connecting members 862. Connecting members 862 connect to a mating connecting members 896 of light source cables 894. Cables 894 connect to a light source (not shown). Light emitters 810 forms the gripping surfaces of arms 870, and provide focused or diffuse light. It should be appreciated that light emitters 810 may provide light for inspection, as well as transillumination. In the case of inspection the light is used to inspect a work area before proceeding with a further operation. With regard to transillumination, the light may be use to examine a bodily structure. For instance, a vein may be transilluminated to identify a blood clot before clamping and cutting.

FIGS. 13 and 14 show a multi-purpose lighting device 108. Device 108 is generally comprised of a light delivery portion 902 and a handle portion 970. Light delivery portion 902 includes a light distributor 960 and a light emitter 910A. Handle portion 970 includes a central housing 972, a connecting member 974 and an endcap 976. As shown in FIG. 14, handle portion 970 houses a power source 950 (e.g., batteries), a light source 952 (e.g., light bulb), a reflector 954, a light filter 956 and a switch means 974. Reflector 954 reflects the light generated by light source 952. Light filter 956 filters the reflected light before it exits through the open end of connecting member 974. Light source 952 is turned on and off by switch means 978. It should be noted that endcap 976 may include a contact member for completing a circuit for powering light source 952.

It should be appreciated that connecting member 974 is dimensioned to receive a light distributor 960, as best seen in FIG. 14. Accordingly, a variety of different types of light delivery portions 902 can be used in combination with handle portion 970, wherein handle portion 970 provides a light source. For instance, light delivery portion 902 may include a light emitter 910A in the form of an illuminated ball (FIG. 13). The surface of the ball may be covered with cotton to form an illuminated cotton swab suitable for obtaining a culture. Alternatively, light delivery portion 970 may include a light emitter 901 B in the form of an end light (FIG. 14), a light emitter 910C in the form of an illuminated tongue depressor (FIG. 14), and a light emitter 910D in the form of a transillumination tray (FIG. 14), similar to tray 104, described above. Through the use of a variety of attachable light delivery portions 902, device 108 serves a wide range of functions. The light delivery portion or a sleeve fitting over the light delivery portion may be disposable for convenient reuse.

It should be appreciated that the light delivery portions shown in FIGS. 13 and 14 are shown solely for the purpose of illustrating a preferred embodiment of the present invention. In this respect, other types of light delivery portions, serving functions similar to those of the illustrated embodiments, are also contemplated. Moreover, it should be appreciated that the portable light source housed in the handle portion may be suitably replaced by a remote light source (e.g., see FIG. 4A), with a light pipe for conveying the light therefrom.

Referring now to FIG. 15A, there is shown a lighting device 109, which functions as a flexible and formable "trouble light." Lighting device 109 is generally comprised of a light delivery portion 1002 and a handle portion 1070. Light delivery portion 1002 includes a light distributor 1060 and a light emitter 1010. Light distributor 1060 includes a connecting member 1062 for connecting light distributor 1060 to handle portion 1070. It should be noted that in a preferred embodiment of the present invention, light distributor 1060 is flexible. As seen in the cross-sectional view of FIG. 15B, light distributor 1060 is comprised of a light pipe member 1063, a translucent or colored outer sheath 1061 and a formable wire 1065. Formable wire 1065 allows light distributor 1060 to be bent or positioned in a suitable manner. Light emitter 1010 is detachable from light distributor 1060 to provide a variety of multi-purpose light emitters. In the embodiment shown in FIG. 15A, light emitter 1010 takes the form of a glowing tip, which is rotatable to alter the focus, size or light intensity of lighted area 1004.

Handle portion 1070 is similar to handle portion 970, described above. In this regard, handle portion 1070 includes a central housing 1072, connecting member 1074, endcap 1076, and a switch means 1078. Handle portion 1070 houses a light source and a power source. It should be appreciated that handle portion 1070 is suitably replaced by a light pipe 1090 of conventional light source. Light pipe 1090 includes a cable 1094 and a mating connecting member 1096, which mates with connecting member 1062.

Device 109 may optionally include a rigid support member 1050 to keep light distributor 1060 from changing positions. Support member 1050 includes an arm 1052 and clamp 1054. Clamp 1054 engages with light distributor 1060.

Referring now to FIG. 16A, there is shown a formable "rope" lighting device 1101, which is similar to the lighting device shown in FIGS. 15A and 15B. Lighting device 1101 is generally comprised of a light distributor 1160 and light emitters 1110. Light distributor 1160 includes a connecting member 1162 for connecting light distributor 1160 to a light source (not shown). It should be noted that in a preferred embodiment of the present invention, light distributor 1160 is formed of a flexible optic light guide. As seen in the cross-sectional view of FIG. 16B, a protective outer sleeve 1170 covers light distributor 1160. Outer sleeve 1170 is preferably formed of a translucent or transparent material. An optional formable wire 1150 extends between light distributor 1160 and outer sleeve 1170, to permit lighting device 1101 to hold its shape once bent to a suitable position. Light emitters 1110 provide difflluse light D along length L, in addition to a focused beam of light B at the free end of lighting device 1101. It should be noted that at optional lens may be provided at the free end of lighting device 1101 to focus light B from light emitters 1110 in a desired pattern.

Figure 17:
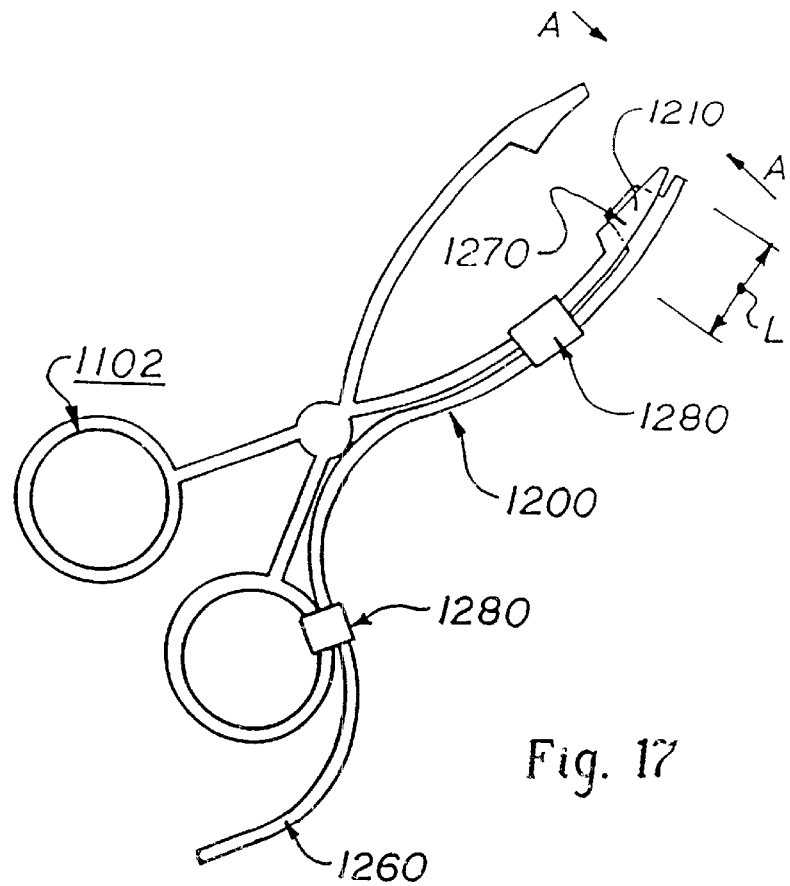
FIG. 17 is a top view of a trans-illuminating forceps including an attachable light delivery system.

Referring now to FIG. 17, there is shown a trans-illuminating pickup or forceps 1102 having an attachable light delivery system 1200. Arrows A illustrate the direction in which forceps 1102 is movable. Light delivery system 1200 is generally comprised of a light distributor 1260 and a light emitter 1210. Light distributor 1260 includes connecting members (not shown) for connecting light delivery system 1200 to a light source (not shown). Light distributor 1260 preferably takes the form of an optic light guide cable, which may be either rigid or flexible. Attachment members 1280 connect light distributor 1260 to forceps 1102. In a preferred embodiment of the present invention attachment members take the form of clips. An opening 1270 is formed at the tip end of one arm of forceps 1102. Opening 1270 is dimensioned to receive light emitter 1210. Light emitter 1210 provide light along length L. It should be appreciated that a second opening 1270 may be formed in the second arm of forceps 1102, in order to receive a second light emitter.

Figure 18:
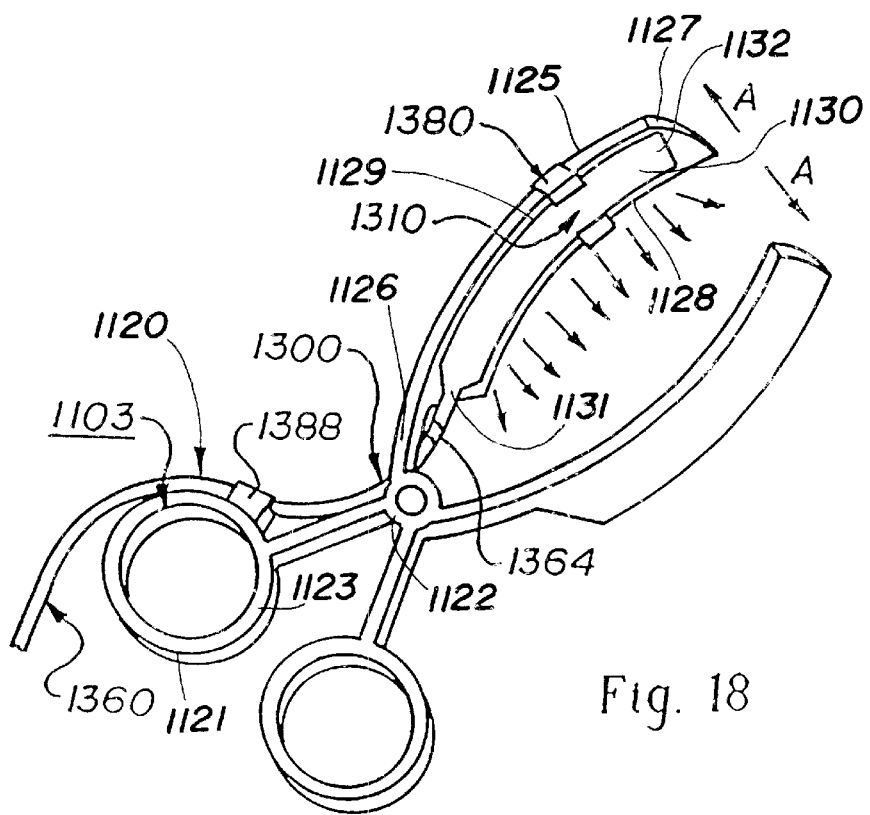
FIG. 18 is a perspective view of a trans-illuminating retractor including an attachable light delivery system.

Referring now to FIG. 18, there is shown a trans-illuminating retractor 1103 having an attachable light delivery system 1300. Arrows A illustrate the directions in which retractor 1103 is movable. Light delivery system 1300 is generally comprised of a light distributor 1360 and a light emitter 1310. Light distributor 1360 includes connecting members (not shown) for connecting light delivery system 1300 to a light source (not shown). Light distributor 1360 preferably takes the form of an optic light guide cable, which may be either rigid or flexible. A connector 1364 is provided to connect and interface light distributor 1360 with light emitter 1310. Attachment members 1380 and 1388 connect light delivery system 1300 to forceps 1103. In a preferred embodiment of the present invention attachment member 1380 takes the form of a clip. Light emitter 1310 extends along the inner surface of the retractor arms.

The retractor 1103 shown in FIG. 18 includes a handle 1120 having opposite ends 1121 and 1122 and a gripping surface 1123 for contact with the hand of a user.

A retractor arm 1125 is in the shape of an elongated blade having a planar lengthwise dimension and a generally curved cross-sectional shape as shown. The distal end 1126 of the retractor arm 1125 is connected to the handle end 1122. Extending between the distal end 1126 and the proximal end 1127 of the retractor blade 1125 is a blade inner surface 128.

Light emitter 1310 is also in the shape of an elongated blade and extends along the length of the retractor blade 1125 for illuminating the retractor blade along all or a portion of the length thereof as shown. The retractor blade 1125 also acts as a back reflector for the light emitter blade 1310, which has inner and outer surfaces 1129 and 1130 extending between its distal and proximal ends 1131 and 1132.

Both the retractor blade 1125 and light emitter blade 1310 extend at an angle with respect to the handle 1120. The distal end 1131 of the light emitter 1310 defines an illumination input end portion to which the connector 1364 is coupled to optically couple the light emitter to a light source for emission of the light from the light emitter to illuminate the retractor blade along all or a portion of the length thereof as schematically shown in FIG. 18.

FIGS. 19A and 19B illustrate a spring-formed "rope" lighting device 1 104. lighting device 1104 is generally comprised of a light distributor 1460 and a light emitter 1410. Light distributor 1460 interfaces with a self-contained miniature light source unit 1490. Light source unit 1490 includes a light source (e.g., LED, incandescent light, laser diodes or the like) and a power source (e.g., a button battery cell or the like). The miniaturization and portability of light source unit 1490 allows lighting device 1104 to be arrangeable within a bodily structure, such as a body cavity. Alternatively, a remote light source may substitute for self-contained light source unit 1490. It should be noted that in a preferred embodiment of the present invention light distributor 1460 is formed of a flexible optic light guide. As best seen in the cross-sectional view of FIG. 19B, a protective outer sleeve 1470 covers light distributor 1460. Outer sleeve 1470 is preferably formed of a translucent or transparent material. A spring 1450 extends between light distributor 1460 and outer sleeve 1470. Spring 1450 may be formed of a material which allows it to return to its original shape after being compressed. Accordingly, spring 1450 has a "memory," which allows for advantageous use of lighting device 1104, as will be described below. Light emitter 1410 provides diffuse light D along length L.

It should be appreciated that while lighting device 1104 is shown with a generally round cross-sectional area, lighting device 1104 may have a cross-sectional area of other shapes, including a square and octagon.

Lighting device 1104 finds particularly advantageous use as a means for holding a cavity open during a surgical procedure. In this regard, lighting device 1104 is compressed (i.e., squeezed) and inserted through an opening into a cavity (e.g., a heart chamber). When the compressive force is removed from lighting device 1104 the "memory" of spring 1450 causes the device to return to its original shape (i.e., spring open). As a result, the cavity opening is conveniently held open during further surgical procedures. It should be appreciated that spring 1450 may be suitably shaped to fit a particular application.

FIGS. 20A and 20B illustrates a smoke evacuation tube 1105 having an integrated light delivery system 1500. Light delivery system 1500 is generally comprised of a light distributor 1560 and light emitters 1510. Light distributor 1560 includes a connecting member 1562 for connecting light distributor 1560 to a light source (not shown). Light distributor 1560 is preferably formed of a flexible optic light guide. As best seen in the cross-sectional view of FIG. 20B, a protective outer sleeve 1574 covers light distributor 1560. Outer sleeve 1574 is preferably formed of a translucent or transparent material. An optional formable wire 1550 extends between light distributor 1560 and outer sleeve 1574, to allow smoke evacuation tube 1105 to hold its shape once arranged in a desired position. Light emitters 1510 provide diffuse light D along length L, in addition to a beam of light B. It should be noted that an optional lens may be provided at the free end of smoke evacuation tube 1105 to focus light B from light emitter 1510 in a desired pattern.

A hollow tube 1570 forms an evacuation chamber 1572 for removing smoke. As best seen in FIG. 20B, hollow tube 1570 surrounds and connects to outer sleeve 1574. Hollow tube 1570 is preferably formed of a translucent or transparent material. It should be appreciated that in an alternative embodiment, sleeve 1574 and tube 1570 are suitably arranged adjacent to each other.

FIGS. 21A and 21B illustrates a suction tube 1106 having an integrated light delivery system 1600. Light delivery system 1600 is generally comprised of a light distributor 1660 and light emitters 1610. Light distributor 1660 includes a connecting member 1662 for connecting light distributor 1660 to a light source (not shown). Light distributor 1660 is preferably formed of a flexible optic light guide. As best seen in the cross-sectional view of FIG. 21B, a protective outer sleeve 1674 covers light distributor 1660. Outer sleeve 1674 is preferably formed of a translucent or transparent material. An optional formable wire 1650 extends between light distributor 1660 and outer sleeve 1674, to permit suction tube 1106 to hold its shape once arranged in a desired position. Light emitters 1610 provide diffluse light D along length L, in addition to a focused beam of light B. It should be noted that an optional lens may be provided at the free end of suction tube 1106 to focus light B from light emitter 1610 in a desired pattern. A hollow tube 1670 forms a suction chamber 1672 for suctioning smoke and other materials. A nozzle 1676 is formed at the free end of hollow tube 1670. As best seen in FIG. 21B, hollow tube 1670 is arranged adjacent and connected to outer sleeve 1674. Hollow tube 1670 is preferably formed of a translucent or transparent material.

FIGS. 22A and 22B illustrates a suction tube 1107 having an attachable light delivery system 1700. Light delivery system 1700 is generally comprised of a light distributor 1760 and light emitters 1710. Light distributor 1760 includes a connecting member 1762 for connecting light distributor 1660 to a light source (not shown). Light distributor 1760 is preferably formed of a flexible optic light guide. As best seen in the cross-sectional view of FIG. 22B, a protective outer sleeve 1774 covers light distributor 1760. Outer sleeve 1774 is preferably formed of a translucent or transparent material. An optional formable wire 1750 extends between light distributor 1760 and outer sleeve 1774, to permit suction tube 1107 to hold its shape once arranged in a desired position. Light emitters 1710 provide diffuse light D along length L, in addition to a beam of light B. It should be noted that an optional lens may be provided at the free end of suction tube 1107 to focus light B from light emitter 1710 in a desired pattern.

A hollow tube 1770 forms a suction chamber 1772 for suctioning smoke and other materials. A nozzle 1776 is formed at the free end of hollow tube 1670. Hollow tube 1770 is preferably formed of a translucent or transparent material. Attachment members 1780 connect hollow tube 1770 to outer sleeve 1774. In a preferred embodiment, attachment member 1780 takes the form of a clip having a pair of gripping members respectively dimensioned to receive hollow tube 1770 and sleeve 1774 (FIG. 22A). However, it should be appreciated that attachment member 1780 may take other suitable forms.

Figures 23A, 23B:
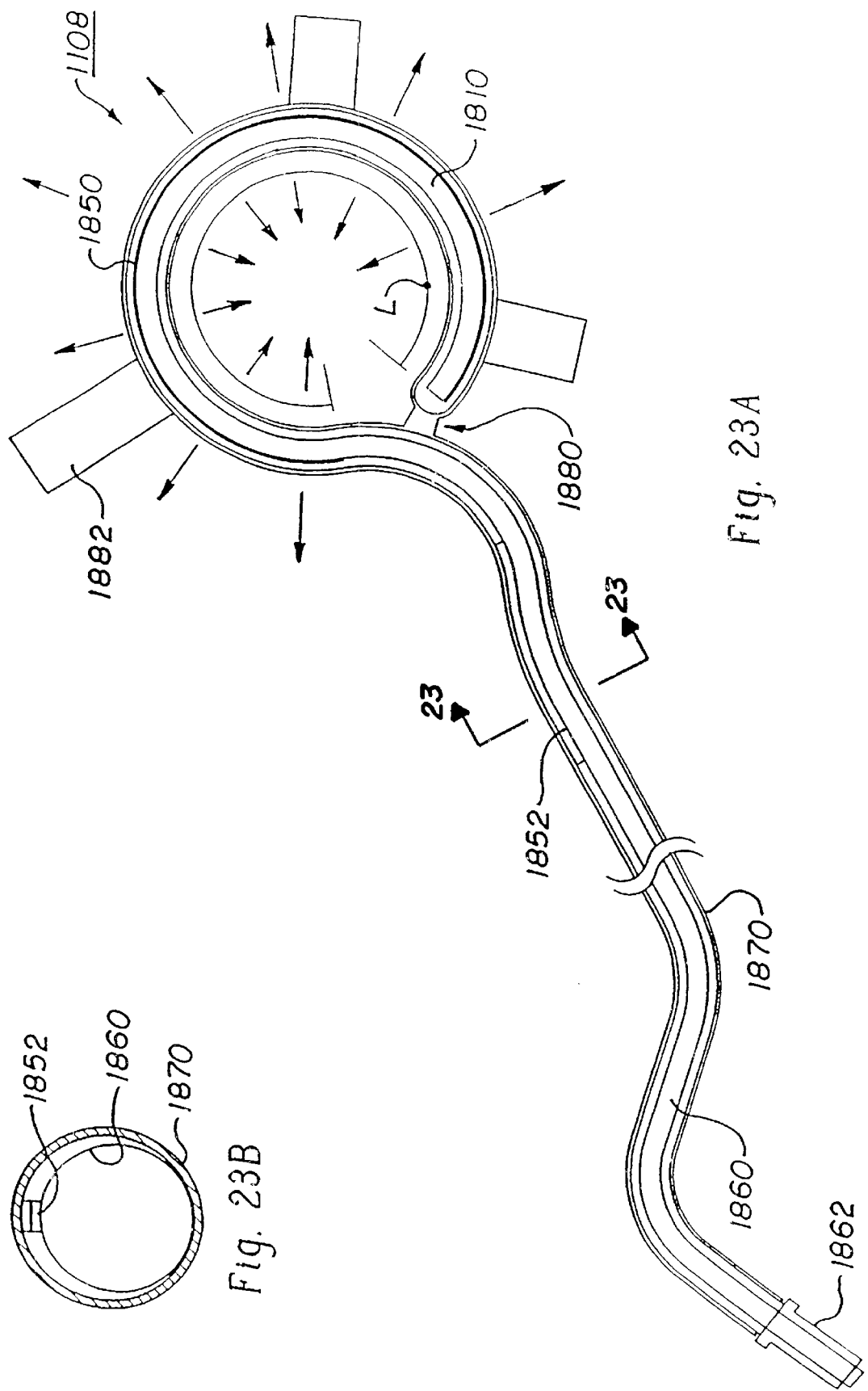
FIG. 23A is a perspective view of a ring-shaped "rope" lighting device.
FIG. 23B is a cross-sectional view of the lighting device taken along line 23—23 of FIG. 23A.

Referring now to FIG. 23A, there is shown a ring-shaped "rope" lighting device 1108. Lighting device 1108 is generally comprised of a light distributor 1860 and light emitters 1810. Light distributor 1860 includes a connecting member 1862 for connecting light distributor 1860 to a light source (not shown). It should be noted that in a preferred embodiment of the present invention, light distributor 1860 is formed of a flexible optic light guide. As seen in the cross-sectional view of FIG. 23B, a protective outer sleeve 1870 covers light distributor 1860. Outer sleeve 1870 is preferably formed of a translucent or transparent material. A custom-formed spring temper wire 1850 extends between light distributor 1860 and outer sleeve 1870. Wire 1850 may be compressed and will return to its original shape. Light emitter 1810 provides light along length L. A fastener 1880 is provided to hold lighting device 1108 in a desired shape. Fastener 1880 may take many suitable forms, including a mechanical fastener or adhesive (e.g., glue). A secondary wire 1852 is provided along a portion of light distributor 1860. Wire 1852 may be malleable or spring temper. Tabs 1882 hold lighting device 1108 in a desired location, and can also be used to retract tissue during a surgical procedure. In a preferred embodiment, tabs 1882 take the form of adhesive tape.

As indicated above, a protective outer sleeve may cover a light transmitting member (e.g., light distributor or light emitter). The purpose of this protective cover is to prevent (1) contaminants (such as blood, body tissue, dirt, oil, grease, paint, etc.); (2) other components (such as adhesive pads, labels, hooks, etc.); or (3) any other material or structure than can cause attenuation, from directly contacting the light transmitting member and preventing proper operation thereof. In this regard, the protective cover allows light to pass through the light transmitting member with minimal disturbance to internal reflection of light travelling therethrough. When contaminants or components are in direct contact with the light transmitting member, they interfere with the proper internal reflection within the light transmitting member. In particular, the angle of reflection of light travelling through the light transmitting member is changed. In the case where there is no air gap, or virtually no air gap between the contaminant/components and the surface of the light transmitting member, optical energy of the light propagating through the light transmitting member (e.g., originating from a 300 Watt light source) is absorbed by the contaminant. As a result, the temperature of the contaminant will increase, possibly to an undesirable level.

It should be noted that the term "cover" as used herein refers to materials providing a film, skin, boundary layer, coating, and the like. Specific examples of suitable materials are discussed below.

Figure 24A:
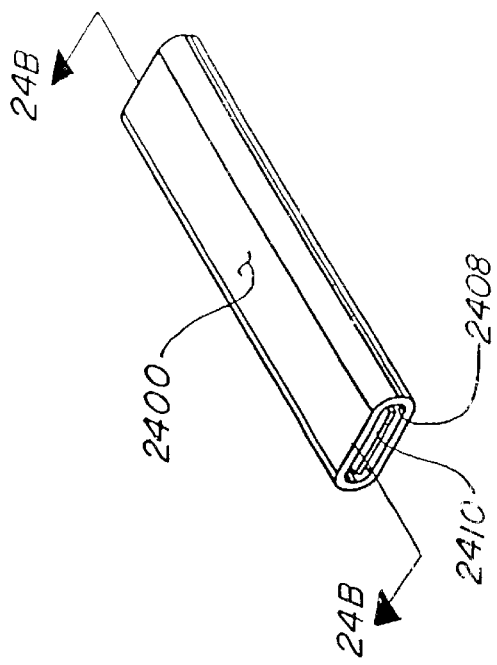
FIG. 24A is a perspective view of a protective cover applied to a light distributor, in accordance with one embodiment of the present invention.
Figure 24B:
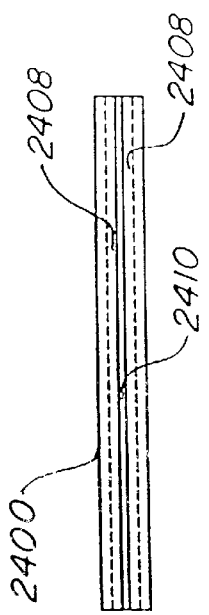
FIG. 24B is a cross-sectional view of the protective cover, taken along line 24B—24B of FIG. 24A.
Figure 24D:
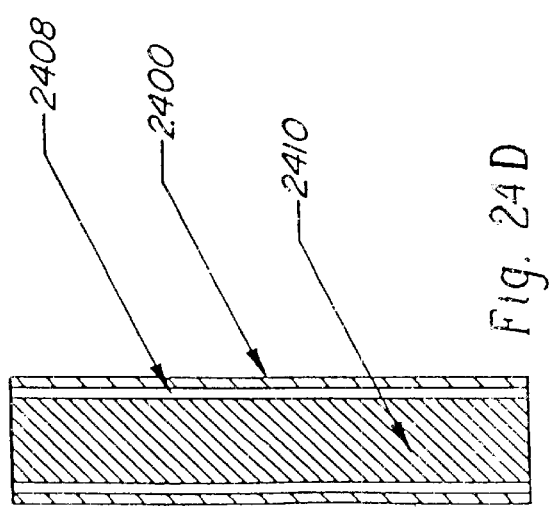
FIG. 24D is a cross-sectional view of the protective cover, taken along line 24D—24D of FIG. 24C.
Figure 24C:
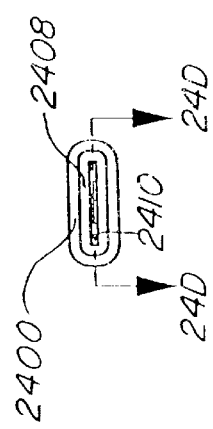
FIG. 24C is an end view of the protective cover shown in FIG. 24A.

Referring now to FIGS. 24A–24D, there is shown a first exemplary embodiment of the protective cover. Protective cover 2400 surrounds a light transmitting member 2410 (e.g., a flexible or rigid light pipe). As best seen in FIGS. 24B–24D, an air interface or gap 2408 is maintained between light transmitting member 2410 and cover 2400. It should be appreciated that the air interface or gap may be microscopic (e.g., a couple of microns) to avoid interference with internal reflection. In this regard, reflections occur at the interface of light transmitting member 2410 and air gap 2408. Cover 2400 may be applied to light transmitting member 2410 in variety of suitable ways, including but not limited to molding, vacuum forming, heat shrinking, and the like.

FIGS. 25A–25D illustrate another embodiment of the protective cover. Protective cover 2500 is generally comprised of a first cover portion 2500A and a second cover portion 2500B, which surround light transmitting member 2510. As best seen in FIGS. 25B–25D, an air interface or gap 2508 is maintained between light transmitting member 2510 and cover 2500. Cover portions 2500A and 2500B are bonded together at interface 2502 to form a unitary protective cover 2500 (FIG. 25C). For instance, glue, a heat seal, or the like are suitable for bonding the cover portions 2500A, 2500B.

In the embodiment shown in FIGS. 26A–26D, the cover takes the form of a coating 2600 that is applied to the surface of light transmitting member 2610. Coating 2600 provides an appropriate index of refraction to maintain a desired internal reflection. The coating 2600 may take many suitable forms, including but not limited to optical coatings with an appropriate index of refraction, and Teflon (R). It will be appreciated that in this embodiment there is no air interface or gap.

The protective cover may be comprised of materials taking a number of suitable forms, including but not limited to glass, plastic, shrink film (e.g., Reynolon (R) shrink film packaging), thin-wall PVC heat shrinkable tubing, metal (e.g., aluminum), cardboard, and the like. The wall thickness of the shrinkable tubing is typically in the range of 0.0002 inches to 0.012 inches. Suitable shrinkable tubing is available from Advance Polymers, Incorporated and RJI International Corporation. Where a heat shrinkable tubing is used, the tubing is fit over the light transmitting member and heat is applied, to shrink the tubing around the light transmitting member.

It should be appreciated that the protective cover may be formed of a translucent, transparent, opaque, or reflective material, or combinations thereof. Thus, a lighting device may include a protective cover that allows some portions of the light transmitting member to emit light or "glow," while preventing other portions of the light transmitting member from emitting light or "glowing." For example, the protective cover may be suitably configured with an opaque section corresponding to one side of a light transmitting member, and with a transparent or translucent section corresponding to the other side of the light transmitting member. In addition, a reflective material may be used as a back-deflector to reflect light as it is traveling through the light transmitting member. Furthermore, it should be appreciated that the protective cover may be formed of a material which diffuses light passing therethrough.

The protective covering may be formed of a material that is generally rigid or generally flexible. Some materials may have a "memory," so that when the protective cover is manually bent and then released, it does not retain its deformed state. Other materials may not have a "memory," and thus will not spring back to their original shape after deformation. It should be noted that materials lacking a memory can be effectively used as a means for positioning and supporting a generally flexible light transmitting member.

Referring now to FIGS. 27A and 27B, there is shown a protective cover 2700 according to another embodiment of the present invention, as applied to a light transmitting member 2710. Protective cover 2700 has a generally tubular shape, and includes an outer surface 2702 and an inner surface 2704. In addition, protective cover 2700 has a closed end 2705 and an open end 2706, with a central body portion 2707 extending therebetween. Closed end 2705 covers the distal end of light transmitting member 2710. Open end 2706 is dimensioned to receive a connector member 2720, which is described below. An air interface or gap 2708 is maintained between protective cover 2700 and light transmitting member 2710.

In the embodiment shown in FIGS. 27A and 27B, light transmitting member 2710 takes the form of a "light rod" which emits light at the distal end of the light transmitting member. In this respect, light emitters form a part of the light transmitting member 2710, along a portion of the distal end, to emit light in a manner appropriate for a particular application.

Connector member 2720 is attached to light transmitting member 2710, and provides an interface 2722 for attaching protective cover 2700. Interface 2722 includes a generally cylindrical engagement wall 2724 and a circular flange 2726. In a preferred embodiment, the outer surface of engagement wall 2724 mates with inner surface 2704 of protective cover 2700. For instance, mating threads may be formed on the outer surface of engagement wall 2724 and inner surface 2704. Alternatively, the outer diameter of engagement wall 2724 may be dimensioned to press-fit within protective cover 2700. Circular flange 2726 acts as a stop to prevent over-tightening of connector member 2720 withing protective cover 2700. In this respect, the front surface of circular flange 2726 engages with the front surface of open end 2706 of protective cover 2700.

Protective cover 2700, in cooperation with connector member 2720, seal a portion of light transmitting member 2710 from contact with contaminants. In a preferred embodiment the portion of the light transmitting member 2710 protected from contaminants will include a portion that emits light on a work area, and is the portion most likely to make contact with contaminants. Protective cover 2700, in combination with connector member 2720, encloses a portion of light transmitting member 2710.

FIGS. 28A and 28B show a protective cover 2800 that surrounds a light transmitting member 2810, and takes the same form as protective cover 2700. In this regard, protective cover 2800 has a generally tubular shape, and includes an outer surface 2802 and an inner surface 2804. In addition, protective cover 2800 has a closed end 2805 and an open end 2806, with a central body portion 2807 extending therebetween. Closed end 2805 covers the distal end of light transmitting member 2810. Open end 2806 is dimensioned to receive a connector member 2820, which is described below. An air interface or gap 2808 is maintained between protective cover 2800 and light transmitting member 2810.

In the embodiment shown in FIGS. 28A and 28B, light transmitting member 2810 also takes the form of a "light rod" which emits light at a distal end thereof.

Connector member 2820 is attached to light transmitting member 2810, and provides an interface 2822 for attaching protective cover 2800. Interface 2822 includes a generally cylindrical engagement wall 2824 and a circular flange 2826. In a preferred embodiment, the outer surface of engagement wall 2824 mates with inner surface 2804 of protective cover 2800. Circular flange 2826 acts as a stop to prevent over-tightening of connector member 2820 within protective cover 2800. In this respect, the front surface of circular flange 2826 engages with the front surface of open end 2806 of protective cover 2800.

In the embodiment shown in FIGS. 28A and 28B, an attachment member 2850 attaches an accessory device 2860 to the lighting device. Attachment member 2850 can take a variety of suitable forms, including adhesive tape, Velcro fasteners, clips, hooks, tabs, clamps, snaps and the like. Moreover, it should be understood that attachment member 2850 may be an integral part of protective cover 2800. In this regard, protective cover 2850 may suitably include molded clips, hooks, tabs or the like, for attachment of an accessory device. Accessory device 2860 can also take a variety of suitable forms, including a medical instrument. In FIGS. 28A and 28B, accessory device 2860 takes the form of a retractor blade.

Since attachment member 2850 is separated from light transmitting member 2810 by protective cover 2800 and air interface or gap 2808, it does not interfere (or minimizes interference) with the propagation of light through light transmitting member 2810 via internal reflection. Consequently, attachment member 2850 does not cause the same problems that are caused by contaminants in direct contact with light transmitting member 2810.

FIGS. 29A and 29B show a protective cover 2900 that is similar in many respects to protective covers 2700 and 2800, described above. Protective cover 2900 surrounds a light transmitting member 2910. In this regard, protective cover 2900 has a generally tubular shape, and includes an outer surface 2902 and an inner surface 2904. In addition, protective cover 2900 has a closed end 2905 and an open end 2906, with a central body portion 2907 extending therebetween. Closed end 2905 covers the distal end of light transmitting member 2910, and includes an optional lens L for focusing the light emitted therethrough in a desired pattern. Open end 2906 is dimensioned to receive a connector member 2920, which is described below. An air interface or gap 2908 is maintained between protective cover 2900 and light transmitting member 2910.

In the embodiment shown in FIGS. 29A and 29B, light transmitting member 2910 also takes the form of a formable rope light which emits light at the distal end thereof. Light transmitting member 2910 is generally flexible. Accordingly, a malleable wire W is provided to hold the shape of light transmitting member 2910 in a desired orientation. Since light transmitting member 2910 is generally flexible, protective cover 2900 is also formed of a flexible material in this embodiment of the invention. For instance, protective cover 2900 may be formed of a flexible PVC material, which will flex along with light transmitting member 2910.

Connector member 2920 is bonded to light transmitting member 2910, and provides an interface 2922 for attaching protective cover 2900. Interface 2922 includes a generally cylindrical engagement wall 2924 and a circular flange 2926. In a preferred embodiment, the outer surface of engagement wall 2924 mates with inner surface 2904 of protective cover 2900. Circular flange 2926 acts as a stop to prevent over-tightening of connector member 2920 within protective cover 2900. In this respect, the front surface of circular flange 2926 engages with the front surface of open end 2906 of protective cover 2900.

Referring now to FIGS. 30A and 30B, there is shown a protective cover 3000 that surrounds a light transmitting member 3010, and takes a form similar to protective covers 2700, 2800 and 2900. In this regard, protective cover 3000 has a generally tubular shape, and includes an outer surface 3002 and an inner surface 3004. In addition, protective cover 3000 has a closed end 3005 and an open end 3006, with a central body portion 3007 extending therebetween. Closed end 3005 covers the distal end of light transmitting member 3010. Open end 3006 is dimensioned to receive a connector member 3020, which is described below. An air interface or gap 3008 is maintained between protective cover 3000 and light transmitting member 3010.

In the embodiment shown in FIGS. 30A and 30B, light transmitting member 3010 takes the form of a generally rigid "ring light" which emits light at a distal end thereof.

Connector member 3020 is attached to light transmitting member 3010, and provides an interface 3022 for attaching protective cover 3000. Interface 3022 includes a generally circular engagement wall 3024. In a preferred embodiment, the inner surface of engagement wall 3024 mates with outer surface 3002 of protective cover 3000.

The invention has been described with reference to a preferred embodiment. Obviously, modifications and alterations will occur to others upon a reading and understanding of this specification. In this regard, it should be appreciated that the present application discloses a numerous exemplary embodiments of the present invention for the purpose of illustrating the present invention. It is contemplated that the various features shown in each embodiment may be combined in a plurality of ways to form further embodiments of the present invention. It is intended that all such modifications and alterations be included insofar as they come within the scope of the appended claims or the equivalents thereof.

Having thus described the invention, it is now claimed:

1. An illuminated surgical retractor comprising a handle having first and second end portions, an elongated first blade portion having one end connected to said second end portion of said handle and another end remote from said one end, an elongated second blade portion extending along the length of said first blade portion, said second blade portion having a first end portion defining an illumination input end portion and a second end portion remote from said illumination input end portion, and a connector coupled to said illumination input end portion, said connector being shaped to optically couple said illumination input end portion to a source of illumination so that at least a portion of one of said first and second blade portions is illuminated.

2. The illuminated surgical retractor of claim 1 wherein said second blade portion is substantially transparent.

3. The illuminated surgical retractor of claim 1 wherein said illuminated portion of one of said first and second blade portions is oriented at an angle with respect to the handle.

4. The illuminated surgical retractor of claim 1 wherein said second blade portion forms a light pipe.

5. The illuminated surgical retractor of claim 4 wherein said second blade portion has a printed pattern on a surface thereof for causing light to be emitted from at least a portion of said second blade portion.

6. The illuminated surgical retractor of claim 5 wherein said printed pattern is selected to produce a predetermined light output from said second blade portion.

7. The illuminated surgical retractor of claim 5 wherein said first blade portion acts as a back reflector for said second blade portion.

8. The illuminated surgical retractor of claim 1 further comprising attachment means for attaching said second blade portion to said first blade portion such that said blade portions are substantially parallel.

9. The illuminated surgical retractor of claim 8 wherein said attachment means comprises clips on one of said blade portions for removably engaging the other of said blade portions.

10. The illuminated surgical retractor of claim 1 wherein said first blade portion includes a generally curved cross-section.

11. The illuminated surgical retractor of claim 1 wherein said second blade portion comprises a light emitter, and said connector connects said light emitter to a light distributor.

12. The illuminated surgical retractor of claim 11 wherein said light distributor comprises an optic light guide cable.

13. The illuminated surgical retractor of claim 12 wherein said cable is rigid.

14. The illuminated surgical retractor of claim 12 wherein said cable is flexible.

15. The illuminated surgical retractor of claim 1 further comprising clips for attaching said second blade portion to said first blade portion.

16. The illuminated surgical retractor of claim 1 wherein said first blade portion comprises a retractor blade and said second blade portion comprises a light emitter.

17. An illuminated surgical retractor comprising a handle having a first handle end portion and a second handle end portion, an elongated first blade section having a first blade proximal end portion and a first blade distal end portion with a first blade inner surface extending between the first blade proximal end portion and the first blade distal end portion, the second handle end portion of said handle connected to the first blade distal end portion of said first blade section, an elongated second blade section having a second blade proximal end portion and a second blade distal end portion with a second blade outer surface extending between the second blade proximal end portion and the second blade distal end portion and a second blade inner surface extending between the second blade proximal end portion and the second blade distal end portion, the second blade distal end portion of said second blade section defining an illumination input end portion, and a connector coupled to the illumination input end portion, said connector shaped to optically couple the illumination input end portion to a source of illumination so that at least one of said first blade section and said second blade section is illuminated substantially the entire length thereof.

18. The illuminated surgical retractor of claim 1 wherein said first blade section includes a generally curved cross-section.

19. The illuminated surgical retractor of claim 17 wherein the handle and the first blade section are oriented generally at an angle with respect to each other.

20. The illuminated surgical retractor of claim 17 wherein said second blade section is substantially transparent.

21. The illuminated surgical retractor of claim 17 wherein said second blade section forms a light pipe.

22. The illuminated surgical retractor of claim 21 wherein said second blade section has a printed pattern on one of said second blade outer surface and said second blade inner surface for causing light to be emitted along substantially the entire length of said second blade section.

23. The illuminated surgical retractor of claim 22 wherein said printed pattern produces a predetermined light output from said second blade section.

24. The illuminated surgical retractor of claim 17 wherein said first blade section acts as a back reflector for said second blade section.

25. The illuminated surgical retractor of claim 17 further comprising attachment means for attaching said first and second blade sections such that said first and second blade sections are substantially parallel.

26. The illuminated surgical retractor of claim 25 wherein said attachment means comprises clips on one of said first and second blade sections for removably engaging the other of said first and second blade sections.

27. An illuminated surgical retractor comprising a handle having a first handle end portion and a second handle end portion and a gripping surface for contact with the hand of the user, an elongated first blade section having a generally planar lengthwise dimension and a generally curved cross-sectional shape and a first blade proximal end portion at a first blade distal end portion with a first blade inner surface extending between the first blade proximal end portion and the first blade distal end portion, the second handle end portion of said handle connected to the first blade distal end portion of said first blade section, a second blade section having a second blade proximal end portion, a second blade distal end portion, a second blade outer surface extending between the second blade proximal end portion and the second blade distal end portion, and a second blade inner surface extending between the second blade proximal end portion and the second blade distal end portion, the second blade distal end portion of said second blade section defining an illumination input end portion, and a connector coupled to the illumination input end portion, said connector shaped to optically couple the illumination input end portion to a source of illumination so that at least a portion of one of said first blade section and said second blade section is illuminated.

28. The illuminated surgical retractor of claim 27 wherein said second blade section is substantially transparent.

29. The illuminated surgical retractor of claim 27 wherein said second blade section forms a light pipe.

30. The illuminated surgical retractor of claim 29 wherein said second blade section has a predetermined pattern on one of said second blade outer and inner surfaces for producing a predetermined light output from at least a portion of said second blade section.

31. The illuminated surgical retractor of claim 30 wherein said first blade section acts as a back reflector for said second blade section.

32. An illuminated surgical retractor comprising a handle having a first handle end portion and a second handle end portion, an elongate first blade section having a first blade proximal end portion and a first blade distal end portion with a first blade inner surface extending between the first blade proximal end portion and the first blade distal end portion, the second handle end portion of said handle connected to the first blade distal end portion of said first blade section, an elongate second blade section having a second blade proximal end portion and a second blade distal end portion with a second blade outer surface extending generally parallel to said first blade section and between the second blade proximal end portion and the second blade distal end portion and a second blade inner surface extending between the second blade proximal end portion and the second blade distal end portion, the second blade distal end portion of said second blade section defining an illumination input end portion, and a connector coupled to the illumination input end portion, said connector shaped to optically couple the illumination input end portion to a source of illumination so that at least one of said first blade section and said second blade section is illuminated substantially the entire length thereof.

33. An illuminated surgical retractor comprising a handle, an elongated blade portion having one end connected to said handle and another end remote from said one end, an elongated substantially transparent light emitter extending along the length of said blade portion, said light emitter having a first end portion defining an illumination input end portion and a second end portion remote from said first end portion, and a connector coupled to said illumination input end portion, said connector shaped to optically couple said illumination input end portion to a source of illumination for emitting light along at least a portion of the length of said light emitter.

34. An illuminated surgical retractor comprising a handle, an elongated blade portion having one end connected to said handle and another end remote from said one end, said blade portion including a generally curved cross-section, an elongated light emitter extending along the length of said blade portion, said light emitter having a first end portion defining an illumination input end portion and a second end portion remote from said first end portion, and a connector coupled to said illumination input end portion, said connector shaped to optically couple said illumination input end portion to a source of illumination for emitting light along at least a portion of the length of said light emitter.

35. The illuminated surgical retractor of claim 1 wherein said second blade portion is disposable, further comprising an attachment member for removably attaching said second blade portion to said first blade portion to permit said second blade portion to be removed and replaced.

36. The illuminated surgical retractor of claim 1 wherein said source of illumination includes at least one of: an incandescent bulb, a neon bulb, a fluorescent tube, a lens end bulb, a line light, a halogen lamp, an arc lamp, an xexon lamp, a light emitting diode, a laser diode, a plasma light, and a laser.

37. The illuminated surgical retractor of claim 1 wherein said second blade portion emits directional light.

38. The illuminated surgical retractor of claim 1 wherein said second blade portion emits diffuse non-directional light and directional light.

39. The illuminated surgical retractor of claim 1 wherein said source of illumination includes a light guide that receives light from a remote light source, and said second blade portion comprises a light emitting panel having a greater width than thickness and top and bottom surfaces, said panel having one or more light emitting areas along the length of one of said surfaces from which light is emitted for illuminating a viewing area in proximity of said retractor.

40. The illuminated surgical retractor of claim 1 wherein multiple light extracting deformities are provided on a surface of said second blade portion for directing light toward a viewing area in proximity of said retractor and reducing the intensity of a directional component of the light toward a viewing angle of a user of said retractor.

* * * * *